United States Patent [19]

Gallant et al.

[11] 4,341,225

[45] Jul. 27, 1982

[54] ELECTROCARDIOGRAPHY SYSTEM

[75] Inventors: Stuart L. Gallant; Samuel Woods; Walter E. Palmer, all of Baltimore, Md.

[73] Assignee: Hittman Corporation, Columbia, Md.

[21] Appl. No.: 174,271

[22] Filed: Jul. 31, 1980

[51] Int. Cl.³ .............................................. A61B 5/04
[52] U.S. Cl. .................................... 128/710; 128/902
[58] Field of Search ............... 128/696, 702, 703, 704, 128/706, 709, 710, 712

[56] References Cited

U.S. PATENT DOCUMENTS

| | | | |
|---|---|---|---|
| 2,684,278 | 7/1954 | Marchand | 128/710 |
| 3,478,364 | 11/1969 | Frank | 128/710 |
| 3,517,662 | 6/1970 | Finch et al. | 128/712 |
| 3,793,626 | 2/1974 | Zambuto | 128/710 |
| 3,868,948 | 3/1975 | Graetz | 128/709 |
| 3,951,135 | 4/1976 | Goldberg et al. | 128/710 |
| 4,037,586 | 7/1977 | Grichnik | 128/731 |

*Primary Examiner*—William E. Kamm
*Attorney, Agent, or Firm*—Fleit & Jacobson

[57] ABSTRACT

An improved electrocardiography system displays and records electrocardiograph (ECG) signals provided on multiple pickup leads attached to a patient. The system has the capability of selectively displaying standard preprogrammed lead configurations or lead groups, and provides the operator with the additional capability of programming selected leads from various groups to form a "monitor group". Selected ECG signals are routed to a four-channel oscilloscope and a three-channel strip-chart recorder, the system providing the operator with a "freeze" capability such that a signal appearing on one of the oscilloscope channels may be displayed in a stationary state on the fourth oscilloscope channel, and subsequently printed out on the strip chart recorder. The system further provides an "auto lead" capability for fully automated successive recording of test data from leads in successively accessed conventional lead groups, and further provides an "auto cycle" mode of operation for fully automated repetitive recording of test data from selected leads for operator-designated recording times and at operator-designated time intervals.

43 Claims, 29 Drawing Figures

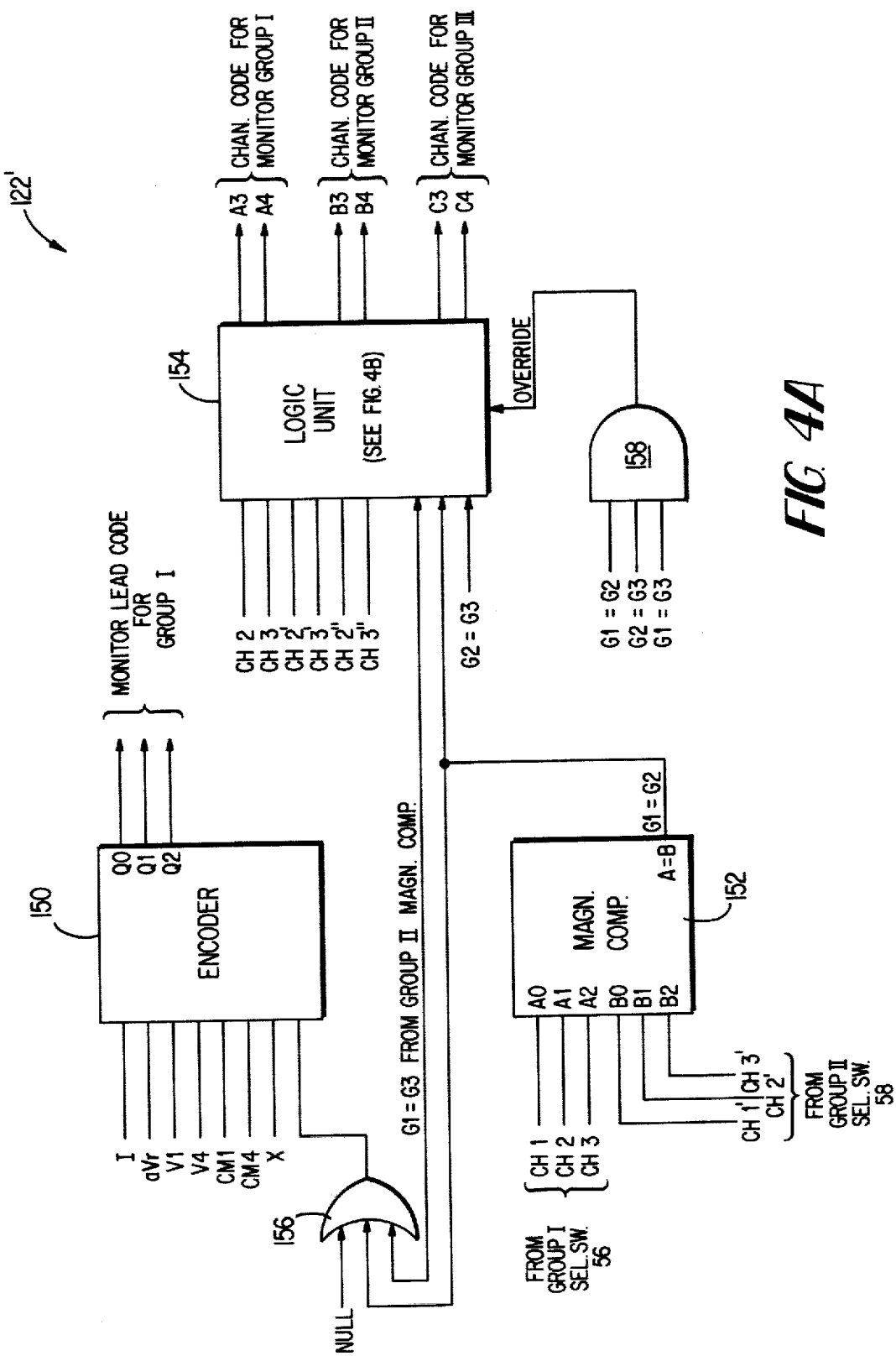

FIG. 4B

| OVERRIDE | |
|---|---|
| A3 | 0 |
| A4 | 1 |
| B3 | 1 |
| B4 | 0 |
| C3 | 1 |
| C4 | 1 |

OUTPUT CHANNEL CODES
01 = CH1
00 = CH2
10 = CH3

| G1 = G3 | CH3 | CH3' | Ā4 G1-3 |
|---|---|---|---|
| 0 | x | x | x |
| 1 | 0 | 0 | 1 |
| 1 | 0 | 1 | 1 |
| 1 | 1 | 1 | 0 |

| G1 = G2 | CH3' | CH3" | B̄4 G2-3 |
|---|---|---|---|
| 0 | x | x | x |
| 1 | 0 | 0 | 1 |
| 1 | 0 | 1 | 1 |
| 1 | 1 | 1 | 0 |

| G2 = G3 | CH3" | CH3 | C̄3 G3-3 |
|---|---|---|---|
| 0 | x | x | x |
| 1 | 0 | 0 | 1 |
| 1 | 0 | 1 | 1 |
| 1 | 1 | 1 | 0 |

| G1 = G3 | CH2 | CH2' | Ā3 G1-2 |
|---|---|---|---|
| 0 | x | x | x |
| 1 | 0 | 0 | 1 |
| 1 | 1 | 0 | 1 |
| 1 | 1 | 1 | 0 |

| G1 = G2 | CH2' | CH2" | B̄3 G2-2 |
|---|---|---|---|
| 0 | x | x | x |
| 1 | 0 | 0 | 1 |
| 1 | 1 | 0 | 1 |
| 1 | 1 | 1 | 0 |

| G2 = G3 | CH2" | CH2 | C̄3 G3-2 |
|---|---|---|---|
| 0 | x | x | x |
| 1 | 0 | 0 | 1 |
| 1 | 1 | 0 | 1 |
| 1 | 1 | 1 | 0 |

| FRONT PANEL SWITCHES SELECTED | 1/2V ENABLES | OUTPUTS A | B | C |
|---|---|---|---|---|
| X20 | X | 1 | 1 | X |
| X20 and 1/2 V | 1 | 1 | 1 | X |
| X10 | X | 1 | 0 | X |
| X10 and 1/2 V | 1 | 1 | 0 | X |
| X5 | X | 0 | X | 1 |
| X5 and 1/2 V | 1 | 0 | X | 1 |
| X20 and 1/2 V | 0 | 1 | 0 | X |
| X10 and 1/2 V | 0 | 0 | X | 1 |
| X5 and 1/2 V | 0 | 0 | X | 0 |

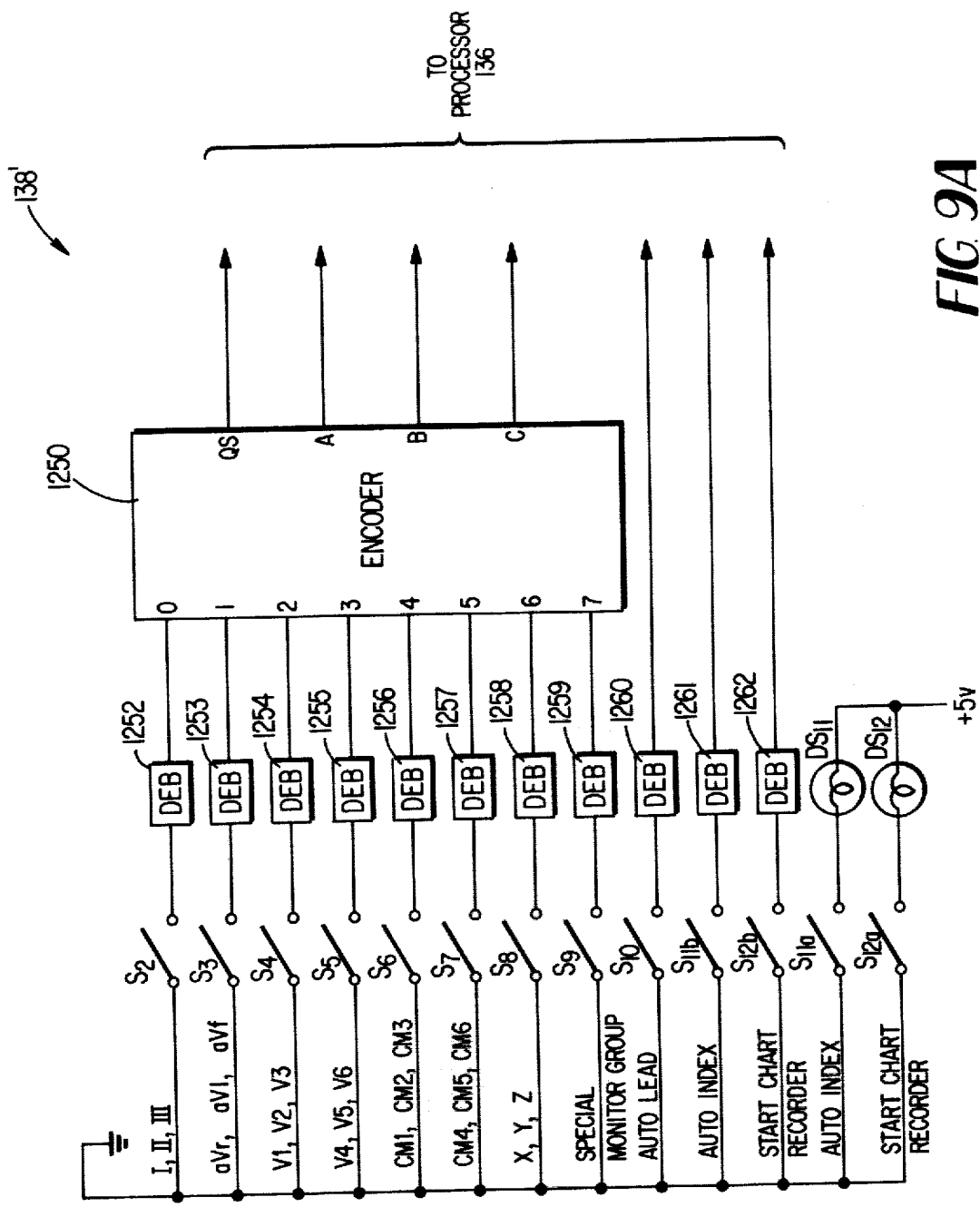

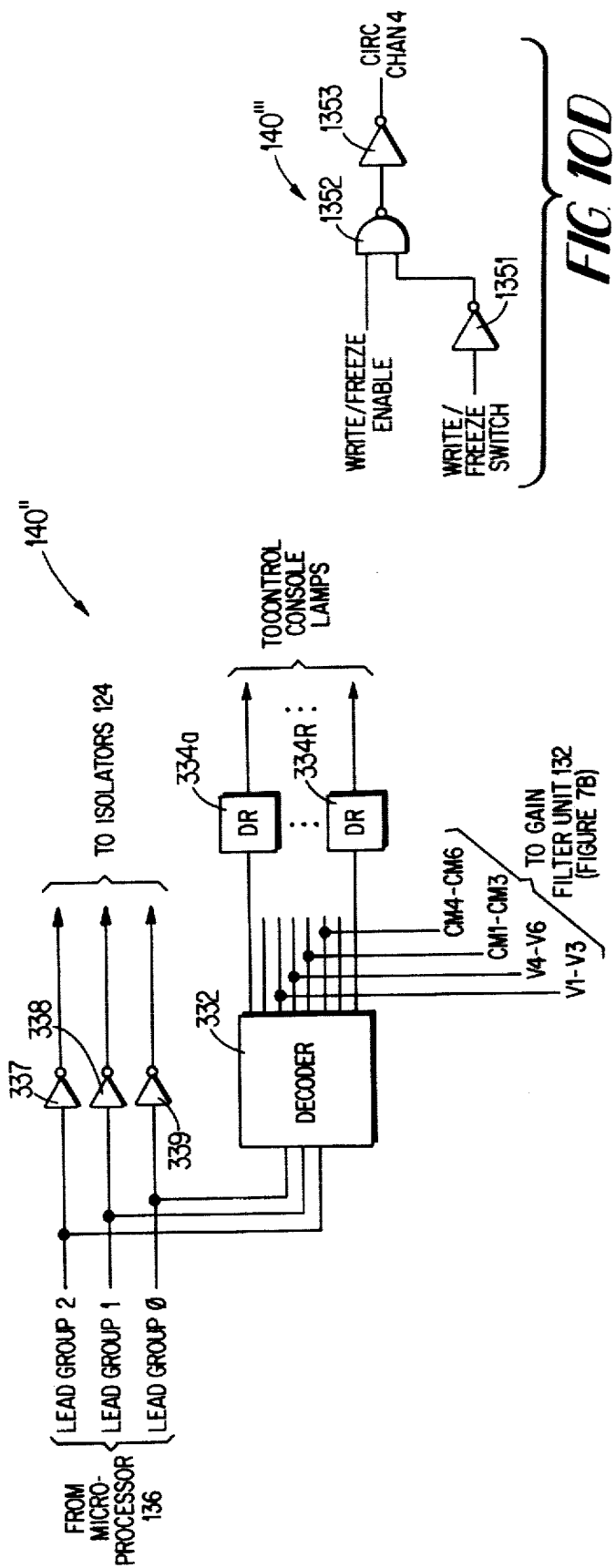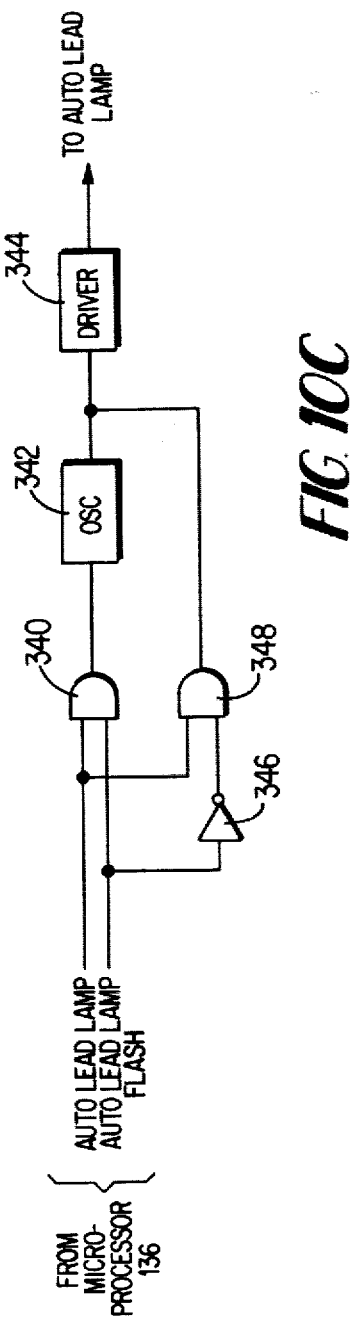
FIG. 10D
FIG. 10C

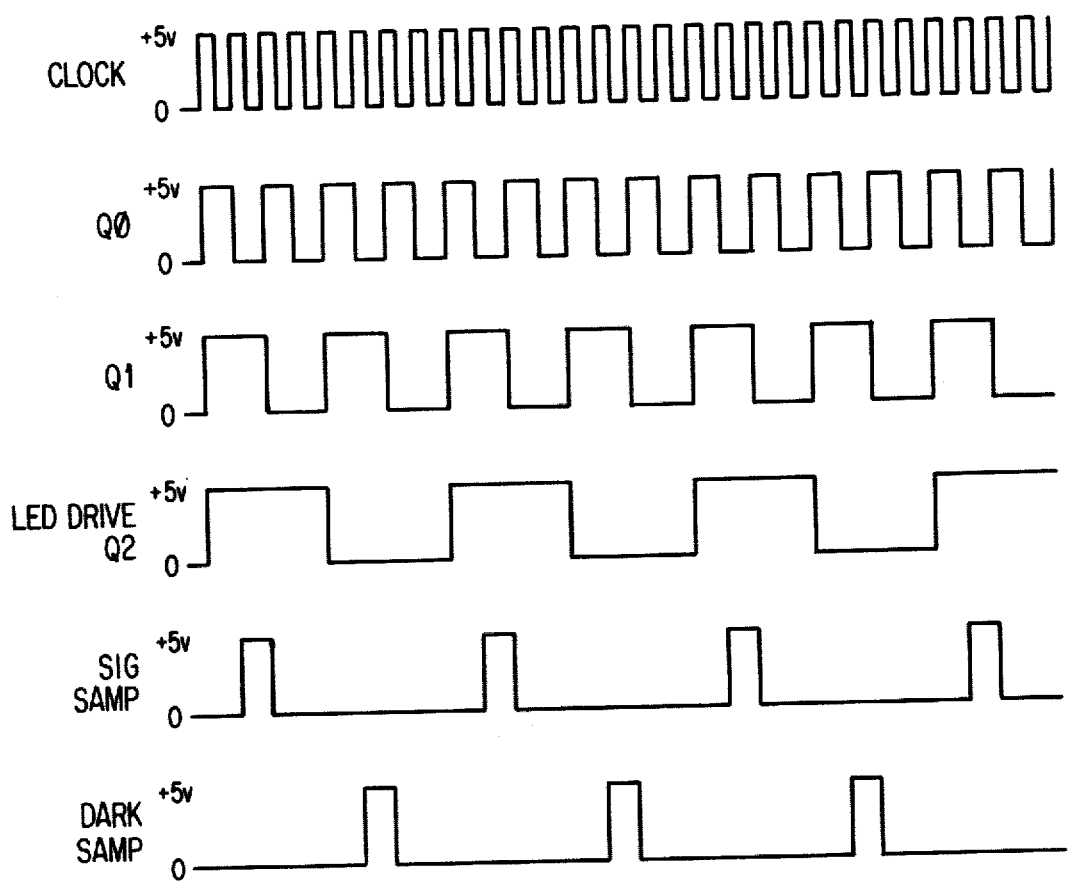

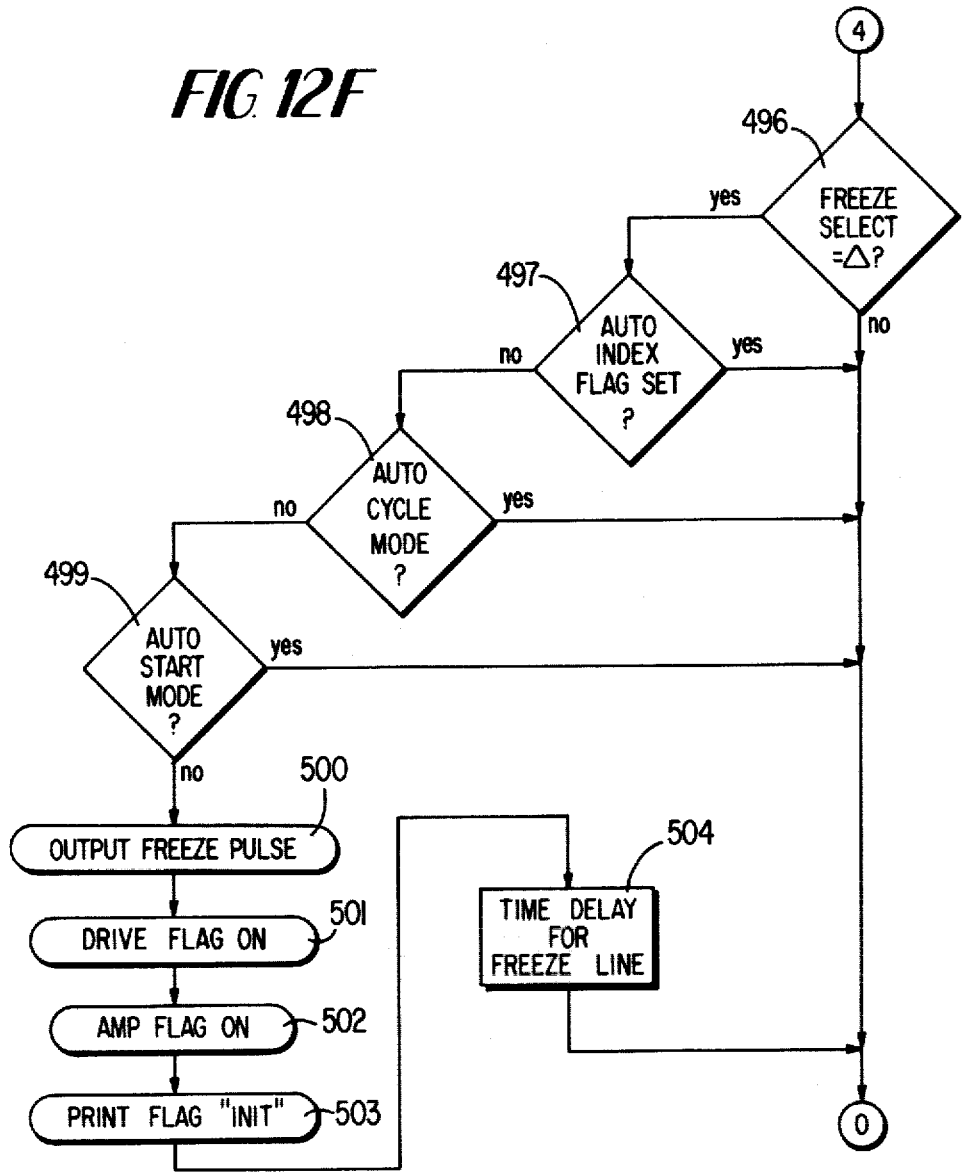

4,341,225

ELECTROCARDIOGRAPHY SYSTEM

BACKGROUND OF THE INVENTION

1. Field of the Invention

The present invention relates to an improved electrocardiography system which displays and records electrocardiograph signals and, more specifically, to a multiple pickup electrocardiography system designed so that medical personnel may easily select various combinations of pickup leads to be viewed and recorded on various respective channels during the electrocardiographic test process.

2. Description of the Prior Art

Electrocardiography has become an important diagnostic tool for the medical profession. Moreover, recently it has become important when coupled with the administration of a stress test in conjunction with a treadmill, or the like. Such stress tests are performed not only on patients who have a history of cardiac disease, but also on otherwise healthy patients during a general examination or during an examination related to another physiological problem.

There are currently available systems which, when properly connected to the patient undergoing the stress test, provide a visual display and paper copy record of the electrocardiography results of the stress test. However, such systems require that medical personnel continuously monitor the apparatus for various reasons. For example, it is necessary that such personnel be continually present during the administration of the stress test so that various lead combinations may be connected properly to the readout devices, and then reconfigured to obtain new data readout. Needless to say, this involves an extreme waste of the time of the medical personnel.

Furthermore, prior art systems involve the manual reconfiguration of the test electrode leads, and this also involves the expenditure of much time. If data readout is continuous, as is often the case, the data output is voluminous. This poses a problem when it comes time for the data to be correlated to specific events of the test. As a result, it is extremely difficult to quickly analyze test data.

Typically, in such electrocardiography systems, a large number of electrode leads are connected to the patient, but only a few (for example, three) of these electrode leads are connected to the display and chart recorder for derivation of data. Moreover, the attending physician or test administrator often finds it necessary, in the course of the test, to connect different leads to the display and chart recorder so as to be able to view a different set of derived data. In this respect, prior art systems are burdened by the necessity of strictly manual reconfiguration (disconnection and connection) of the electrode test leads so as to provide new test lead data for display and recording. This involves much time, and accordingly leaves much to be desired in terms of efficiency of operation.

To summarize, the systems of the prior art are limited to those systems by means of which strictly manual electrocardiographic test administration can take place. That is to say, excessive time expenditure and inefficiency are inherent in the systems of the prior art.

SUMMARY OF THE INVENTION

The present invention relates to an improved electrocardiography system which displays and records electrocardiograph signals and, more specifically, to a multiple pickup electrocardiography system designed so that medical personnel may easily select various combinations of pickup leads to be viewed and recorded on various respective channels during the electrocardiographic test process.

More specifically, the present invention provides a multi-channel electrocardiography stress test system which is intended for use with exercise equipment, such as a treadmill, bicycle, or the like, and which serves to record the electrical activity of the heart as the patient is exercising vigorously.

In accordance with the present invention, the attending physician or test administrator is provided with the capabilities of observing the electrocardiogram being made during the exercise testing, and of selectively recording the electrocardiogram in hard-copy format for later review and for a permanent record.

The present invention is intended for use with a plurality of leads attached to the patient, and provision is made for selective display of standard pre-programmed lead configurations or lead groups. In addition, the user may program selected leads into a "monitor group", so that any of the conventional twelve leads, precordial (CM) leads, or vector ECG leads may be grouped into non-standard combinations and selected for display. Moreover, such lead selection and "monitor group" selection are performed in a quick and efficient manner merely by the pressing of one or more buttons, or the flipping of one or more selection switches, conveniently located on the control console of the unit.

In the system of the present invention, the selected electrocardiogram signals are routed to a four-channel memory oscilloscope and a three-channel strip-chart recorder. A freeze capability is provided such that a signal appearing on one of the three channels of the oscilloscope may be displayed in a stationary state ("frozen") on the fourth channel, and subsequently printed out on the strip chart recorder. In this manner, the attending physician or test administrator may save the test data derived from the patient during a particular phase of the test. Moroever, such saved test data can be easily visually compared with subsequent test data derived from subsequent phases of the test. Such a capability has obvious advantages relative to test data analysis and patient diagnosis.

The present invention can be used with fourteen individual ECG leads to provide a standard twelve-lead group, a modified precordial lead group, or a Frank orthogonal lead group. Additionally, as previously stated, a special monitor capability is provided to permit selection of up to three leads from the above groups to constitute an individualized monitor group. Switches are provided to permit the operator to select, for automatic display and recording, data from any or all of the above three lead groups, as well as to select the specialized monitor group for automatic display and recording, if desired.

The system of the present invention has the further capability of fully automated repetitive recording of test data from the selected electrode leads. That is to say, as a result of activation of an auto-cycle mode of operation, the system will automatically turn on the chart recorder with a predetermined frequency (in the preferred embodiments, every 1, 2, 3, 4 or 5 minutes) and data from the selected lead group will be recorded. Moreover, the data from each selected lead group will be recorded for a given length of time (in the preferred embodiment, from 1 to 19 seconds), such given length of time being predesignated by setting of a switch on the control console of the system. It is to be noted that, as a result of this feature of the present invention, periodic manual operation by the medical personnel, in order to document the patient's exercise electrocardiogram at specific intervals during the exercise stress test, is rendered unnecessary.

Finally, the system of the present invention has the capability of providing, both on command and in an automated manner, calibration data signals to the chart recorder so as to provide a convenient benchmark for use by the attending physician or test administrator in analyzing data recorded on the chart recorder.

Therefore, it is an object of the present invention to provide an improved electrocardiography system which displays and records electrocardiograpic signals and, more specifically, a multiple pickup electrocardiography system designed so that medical personnel may easily select various combinations of pickup leads to be viewed and recorded on various respective channels during the electrocardiographic test process.

It is a further object of the present invention to provide an improved electrocardiography system which permits the medical personnel to select, merely by pressing a button, a specific conventional lead group from which electrocardiography test results can be derived.

It is a further object of the present invention to provide an improved electrocardiography system which permits medical personnel to predesignate unconventional combinations of individual leads as a special monitor group, and to select, by merely pushing a single button, such monitor group for data derivation, display and recording.

It is a further object of the present invention to provide an electrocardiography system which employs both a multi-channel chart recorder and a multi-channel memory oscilloscope to permit the medical personnel to have both a visual display and a permanent record of the electrocardiogram.

It is a further object of the present invention to provide an electrocardiography system wherein the operator, by merely pushing a button, can freeze and save data displayed on a particular channel for future observation and use.

It is a further object of the present invention to provide an electrocardiography system which will automatically perform a pickup lead sequencing operation, by means of which the system, in a completely automated manner, sequences through various lead groups, as predesignated by the operator, so as to derive data for display on respective channels of the chart recorder and memory oscilloscope.

It is a further object of the present invention to provide an electrocardiography system which will automatically turn on and run the chart recorder at preselected intervals and for a predesignated duration so as to automatically/periodically record data from a selected lead group during the test process.

Finally, it is a further object of the present invention to provide an electrocardiography system which will generate, either on demand or in automated manner, a calibration signal for display on the chart recorder and memory oscilloscope for use by the attending physician or test administrator in analyzing test data recorded and displayed thereon.

The above and other objects that will hereinafter appear, and the nature of the invention, will be more clearly understood by reference to the following description, the appended claims and the accompanying drawings.

BRIEF DESCRIPTION OF THE DRAWINGS

FIG. 4A is a block diagram of a representative portion of the program monitor group select 122 of FIG. 3;

FIG. 4B is a truth table corresponding to the operation of logic unit 154 in the program monitor group select of FIG. 4A;

FIGS. 9A and 9B are diagrams of the microprocessor interface unit 138 of FIG. 3;

FIGS. 10A through 10D are diagrams of the microprocessor interface unit 140 of FIG. 3, while FIG. 10E is a timing diagram relating to FIG. 10A;

FIGS. 12A-G are flow charts of the operations performed by the microprocessor 136 of FIG. 3.

DETAILED DESCRIPTION

Figure 1:
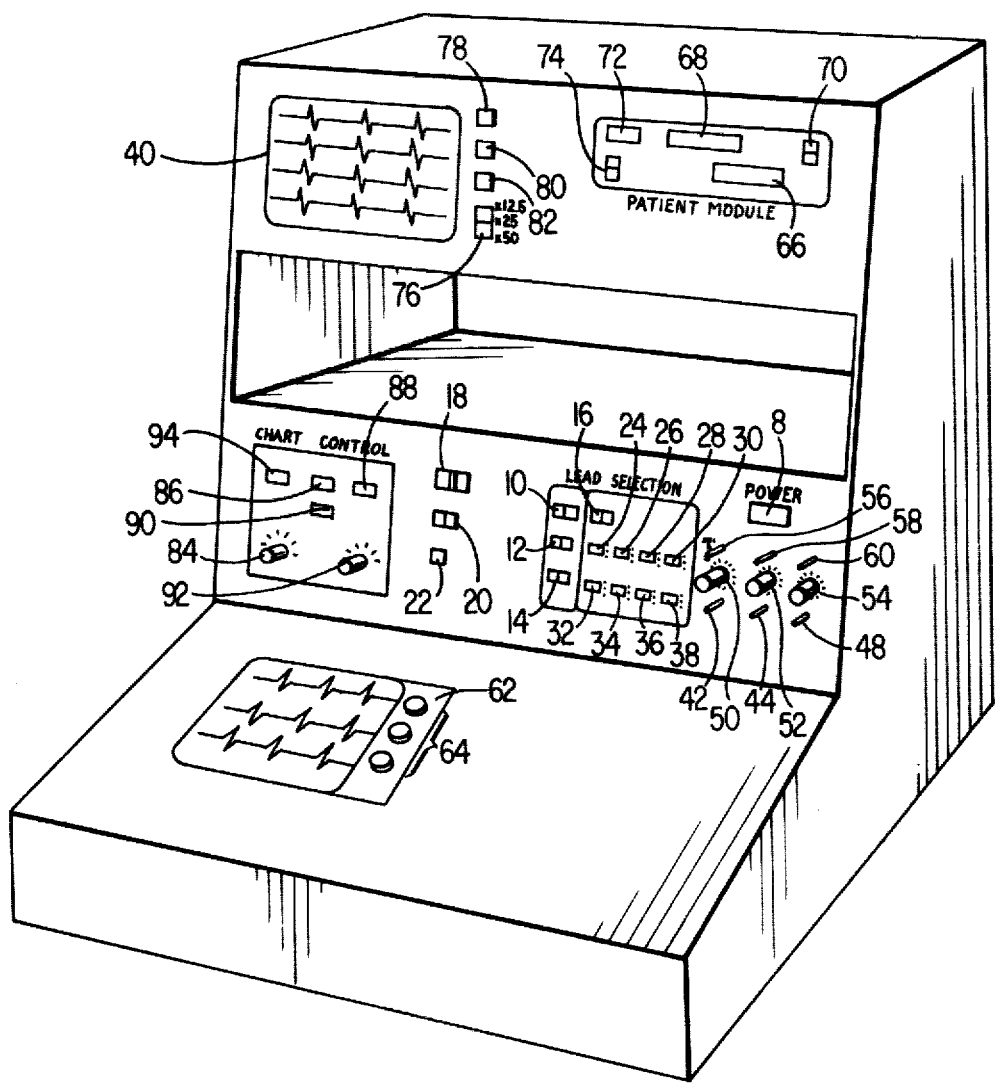
FIG. 1 is a perspective of the control console empolyed in the present invention.

FIG. 1 is a perspective of the control console employed in the present invention, and will now be explained in order to point out the various controls and functions that are provided by the system of the present invention.

Each major control on the console has an indicator light associated with it to indicate to the operator the specific function selected. Certain indicator lights are controlled by a microprocessor so as to indicate that the desired function has actually been detected by the system.

A main power switch 8 is provided to apply power to the inventive system. The remaining switches and buttons on the control console are divided into those pertaining to lead selection, those pertaining to chart control, and those pertaining to oscilloscope control.

Considering the lead selection function, a thumbwheel switch 10 permits the operator to choose a time duration (of from 1 to 19 seconds) for automated recording of each lead group. An automatic lead switch 12, when depressed, automatically and sequentially records data from specifically selected lead groups or groups in accordance with an "automatic electrocardiogram" mode of operation. Switch 14 serves to turn on or off input ECG amplifiers, to which input signals are provided by respective ECG leads. This latter feature is highly important since, when the patient is being connected to or disconnected from the electrocardiography system, turning off the amplifiers totally eliminates noise on the monitor or chatter on the recorder stylus. An artifact filter switch 16 has two individual settings, 35 Hz and 100 Hz, for providing appropriate filtering of the ECG signals depending on the particular test status. For example, the artifact filter can be set to 35 Hz when an exercise electrocardiogram is being performed, since on the 35 Hz setting the frequency response of the recorder will be reduced at the high end, thereby minimizing unwanted motion and harmful noise artifacts. The switch can then be set to the 100 Hz position for a resting electrocardiogram, since harmful artifacts are absent during such a test.

Turning to chart control, switch 18 (a calibration switch) provides the operator with the capability of selecting a tracing sensitivity of 5, 10 or 20 mm/mV for the chart recorder 62. During all automatic modes, a calibration pulse will be generated and traced at the beginning of each lead group tracing, and it will correspond to the specific sensitivity selected. This will be further explained below. Another switch 20 (designated "½-amplitude" or "½ V") permits the operator to reduce the amplitude of the precordial lead tracings by a factor of one-half. When this switch is depressed, a calibration pulse will appear at the beginning of each lead group to show the standardization for that lead group. A further calibration switch 22 (designated "1 mV cal") permits the operator to place a calibration pulse on the chart at any time during the manual electrocardiogram mode of operation. During automatic electrocardiogram mode of operation, a calibration pulse is automatically placed on the chart (by processor command) at the beginning of each pickup lead readout.

Returning to lead selection, a group of switches 24, 26, 28, 30, 32, 34, 36 and 38 permits the operator to select a specific desired lead group for recording and display. Switch 24 corresponds to standard lead data I, II, III; switch 26 corresponds to the augumented lead data aVr, aVl, aVf; and switches 28 and 30 relate to modified precordial lead data, with switch 28 corresponding to lead data CM1, CM2 and CM3, and switch 30 corresponding to lead data CM4, CM5 and CM6. Similarly, switches 32 and 34 relate to the precordial lead data, with switch 32 relating to lead data V1, V2, and V3, and switch 34 relating to lead data V4, V5, and V6. Switch 36 relates to the FRANK orthogonal lead data X, Y, and Z. Switch 38 is a specialized switch for recording of data from the special monitor group of leads. This function will be explained in more detail below.

It is to be noted that, in the automatic electrocardigram mode of operation, depression of automatic lead switch 12 causes the system to automatically and sequentially cycle through the twelve conventional leads I, II, III, aVr, aVl, aVf, V1, V2, V3, V4, V5 and V6 (corresponding to switches 24, 26, 32 and 34).

Switches 42, 44, 46, and 48 provide the operator with total versatility in obtaining the electrocardigram information which is required during the exercise test. Switch 42 is a twelve-lead switch which permits the operator to perform standard twelve-lead data recording during each execution of an automatic recording sequence, as just explained. Switch 44 corresponds to the modified precordial (CM) lead group and, when placed in its "on" position, causes the modified precordial (CM) lead data to be recorded during each execution of the automatic recording sequence. Similarly, switch 46 causes the FRANK (X,Y,Z) lead data to be recorded during each execution of the automatic recording sequence. Additionally, the monitor switch 48 will cause data from three leads selected (in a manner described below) as the monitor group to be recorded during each execution of the automatic recording sequence. Therefore, it is seen that these four switches permit the operator to designate one (or more, in the case of switch 42) of the various lead groups for data recording during the automatic recording sequence.

Three rotary switches 50, 52, and 54 are provided to permit the operator to select the three leads to be included in the special monitor group. As each switch is rotated, and the particular lead group selected, a small colored light, next to each lead group switch 24 through 38, will be illuminated, thereby indicating to the operator the lead that has been selected. More specifically, switch 50 permits the operator to choose from among leads I of switch 24, aVr of switch 26, CM1 of switch 28, CM4 of switch 30, V1 of switch 32, V4 of switch 34, and X of switch 36, as a first monitor lead. Switch 52 permits the operator to choose from among leads II of switch 24, aV1 of switch 26, CM2 of switch 28, CM5 of switch 30, V2 of switch 32, V5 of switch 34, and Y of switch 36 as a second monitor lead. Similarly, rotary switch 54 permits the operator to choose from among leads III of switch 24, aVf of switch 26, CM3 of switch 28, CM6 of switch 30, V3 of switch 32, V6 of switch 34, and Z of switch 36 as the third monitor lead. In the preferred embodiment, the switches 50, 52 and 54 each have an eighth position, selection of which "nulls" that particular switch selection.

Three additional selector switches 56, 58 and 60 provide even more versatility by permitting the operator to choose that channel of the oscilloscope 40 and the chart recorder 62 on which the respective first, second and third special monitor group leads (selected by rotary switches 50, 52 and 54, respectively) will be recorded. Switch 56 is a three-position channel selector switch which permits the operator to place the particular lead selected on rotary switch 50 on channels 1, 2, or 3 of the scope 40 and chart recorder 62. Switch 58 is a three-position channel selector switch which permits the lead selected on rotary switch 52 to be displayed on channel 1, 2, or 3 of the scope 40 and the recorder 62. Additionally, switch 60 is a three-position channel selector switch which permits the lead selected on rotary switch 52 to be displayed on one of the three channels. It is to be noted that, in the instance when the same channel is inadvertently selected on two or more of the three selector switches 56, 58 and 60, nothing will be displayed on that channel.

The strip chart recorder 62 is a conventional three-channel recorder, and controls 64 are provided to permit the stylus of each channel to be centered. Various formats for the recorder 62 are provided to identify the specific lead groups selected. In the automatic twelve-lead ECG recording mode of operation (as selected by switch 12), the lead group being recorded on each channel is indicated (printed) by the chart recorder 62 at the instant that automatic recording of that particular lead group commences. Data from each lead of a given lead group being recorded will appear on a respective channel of the strip chart recorder; e.g., I will appear on channel 1, II will appear on channel 2, III will appear on channel 3, etc. In addition, the strip chart recorder 62 inserts a one millivolt calibration pulse at the beginning of each lead group in order to verify that the recorder sensitivity has been properly adjusted.

Other controls for controlling the chart recorder 62 include a six-position rotary switch 84 which permits the operator to program the chart recorder and the system for the auto cycle mode of operation. That is, control 84 permits programming of the recorder so as to automatically turn on every 1, 2, 3, 4 or 5 minutes, as selected by switch 84, and thereupon to record the selected lead groups for the time selected on switch 10. A write freeze channel switch 86, when actuated, causes the chart recorder 62 to record the information shown on channel 4 of the oscilloscope 40. A direct-/delayed switch 88 permits the operator to select a "direct" position, wherein only real-time ECG data will be written on the chart recorder 62, or to select a "delayed" position, wherein other ECG data (essentially, data just seen on the scope 40) is written on the chart recorder 62. An auto-index switch 90 permits the operator to cause the chart recorder 62 to move automatically to the beginning of the next page on the strip chart. A rotary switch 92 permits the operator to select various chart recorder speeds, such as 12.5, 25 or 50 mm/second. It should be noted that the 12.5 mm per second speed is particularly useful for exercise testing, since the recorder will run at one-half the normal speed (25 mm/second), thereby recording the data on only one-half the normally required amount of paper.

The oscilloscope 40 also has various associated controls, which will now be described. A sweep-speed switch 76 is provided to control the sweep speed of the trace on all three channels. The switch 76 preferably has three positions, corresponding to increasing the sweep speed by factors of 12.5, 25, and 50, respectively. Additionally, freeze controls 78, 80 and 82 are provided for the three channels, respectively. Depressing one of these controls will freeze, on a fourth channel, the ECG complex shown on the channel corresponding to the control depressed. Any ECG complex previously retained in the freeze channel will be automatically erased.

In addition to the displays on the oscilloscope 40 and the strip chart recorder 62, a heart rate indication is provided on a digital readout device 66, which is a continuous eight-beat average digital readout of the heart rate. The readout device 66 preferably has the capability of displaying a heart rate from 20 to 255 beats per minute. By means of a thumbwheel switch 68, the operator can select a high heart rate alarm level in the range of 80 to 250 beats per minute. An audible alarm switch 70 is enabled by setting the switch to the on position. An audible alarm will then sound if the heart rate meets or exceeds the upper limit, set on switch 68, for a period of five seconds or more. Alarm switch 70 also, preferably, has off and reset positions.

As a further readout to the operator, a four-digit continuous time indicator 72 gives the operator a digital readout in minutes and seconds, starting from the depression of the start timing switch 74. The elapsed time meter 72 preferably has a range of from 0 thru 99 minutes, 59 seconds. The start timing switch 74 has a start position at which the elapsed time digital clock 72 begins to count, and a stop position at which the clock 72 will stop and retain the time at the instant the stop position was selected. When the switch 74 is replaced in the start position, the clock 72 will begin to run again from the time at which the stop position was initially selected. Additionally, switch 74 has a reset position which will reset the digital clock 72 to zero.

The various above-described functions are controlled by the control console of FIG. 1 and will be described in more detail in the following detailed description of the inventive system.

Figure 2:
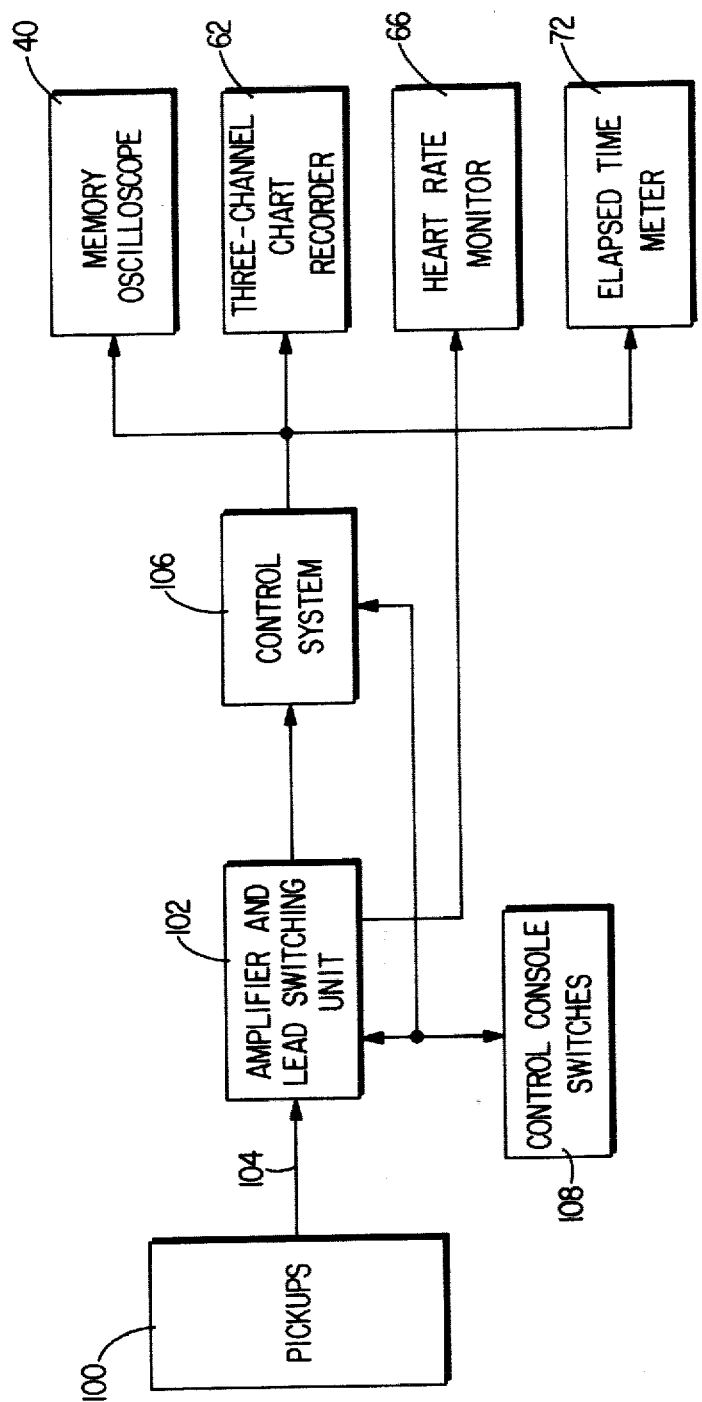
FIG. 2 is a general block diagram of the inventive system.

FIG. 2 is a general block diagram of the system of the present invention. The various electrocardiogram pickups 100, as indicated from the above discussion, preferably comprise fourteen individual electrodes which are placed at various points on the patient's body in accordance with accepted electrocardiogram techniques. In a typical case, electrodes placed at various points on the patient's body will provide electrode lead data designated I, E, M, HCM, V1, V2, V3, V4, V5, V6, RA, LA and LL, that is, thirteen pickup leads, with a fourteenth lead (connected, for example, to the right leg of the patient) being connected to system ground. ECG signals from the pickups 100 are provided to the amplifier and lead-switching unit 102 through leads 104. The amplifier and lead switching unit 102, in a manner to be described in more detail below, buffers the ECG signals, develops the buffered ECG signals into standard ECG lead data, and selects and switchably routes the developed standard ECG lead data, the selection and switchable routing functions being performed in correspondence to the operator inputs provided via control console switches 108. The selected and switchably routed ECG lead data obtained in this manner is then filtered in the control system 106, and is then provided to the memory oscilloscope 40 and the chart recorder 62. In addition, control system 106 provides timing information to the elapsed time meter 72, and the amplifier and lead switching unit 102 provides heart rate information to the heart rate monitor 66.

In the preferred embodiment, memory oscilloscope 40 is of the same general type as Non-Fade Display Module, Model 450-010 (manufactured by Mennen Medical, a/k/a Mennen Greatbatch, Inc. of Clarence, N.Y.). The three-channel chart recorder 62 is, in the preferred embodiment, a chart recorder similar to Model W302XL-117 (manufactured by Astro-Med Division of Atlan-Tol Industries, Inc. of West Warwick, R.I.). Finally, the heart monitor 66 and elasped time meter 72 are preferably any conventional heart rate monitor device and elasped time meter, responsive to conventional digital data input for displaying the decimal equivalent of heart rate and elasped time, respectively.

Figure 3:
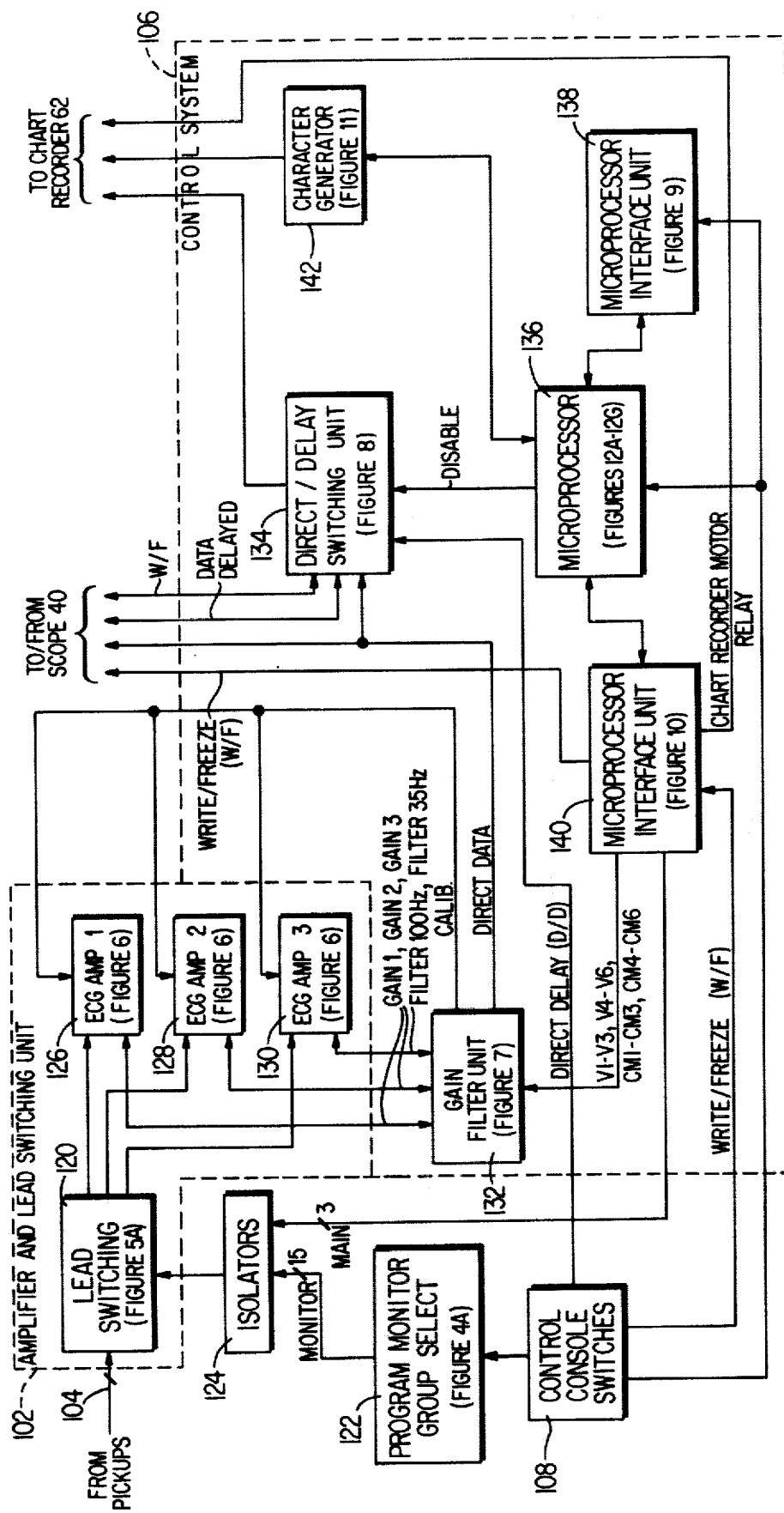
FIG. 3 is a more detailed block diagram of the system of FIG. 2.

FIG. 3 is a more described block diagram of the system of the present invention. As seen in FIG. 3, the amplifier and lead switching unit 102 comprises a lead switching unit 120 and ECG amplifiers 126, 128 and 130. Moreover, control system 106 is seen to comprise gain filter unit 132, direct/delay switching unit 134, microprocessor 136, microprocessor interface units 138 and 140, and character generator 142.

In operation, the signals from the pickups 100 (FIG. 2) are provided on multiline input 104 to lead switching unit 120, which develops standard ECG lead data inputs, and selects three of the inputs for routing to three display channels. This selection is performed based on control signals corresponding to the settings of the control console switches 108, that is, previously described console switches 12, 24-38, and 50-60 (FIG. 1).

More specifically, individual switches 12, 24-38, 50-60 are arranged to provide selection signals as is conventional and known in the art, the latter being provided to program monitor group select unit 122. As described in more detail below, unit 122 performs various counting and logic operations with respect to the selection signals from the control console switches 108, so as to develop logic output signals providing to the lead switching unit 120 via isolators 124. Isolators 124 are conventional isolators, such as electro-optical couplers, and provide the selection signals to the lead switching unit 120, the operation of which will be discussed in more detail hereinbelow. The three standard ECG lead data inputs selected by the lead switching unit 120 are then provided to the ECG amplifiers 126, 128 and 130, which correspond to the three channels of the system. The ECG lead data inputs are amplified therein, and then provided to gain filter unit 132, the operation of which will be explained in more detail below. The gain filter unit 132 processes the standard ECG lead data inputs in accordance with three possible output gains, to provide outputs 5, 10 or 20 times the amplitude of the input thereto. Gain filter unit 132 has, as well, a "one-half gain" capability which permits the amplitude of the precordial lead data to be reduced by one-half. The output signals from the gain filter unit 132 are then provided to the scope 40 and chart recorder 62 (FIG. 1), respectively, and also to a direct/delay switching unit 134 which, in response to input DIRECT/DELAY (D/D) from the control console switches 108, corresponding to the direct/delay switch 88 of the control console of FIG. 1, either directly routes data from the gain filter unit 132 (as displayed on the scope 40) to the chart recorder 62, or effectively delays data displayed on the scope 40 prior to recording on the chart recorder 62. This function will be described in more detail below, with reference to FIG. 8.

The microprocessor 136 receives inputs from the control console switches 108, and also from microprocessor interface units 138 and 140. The microprocessor interface unit 138 contains a programmable timer and various logic elements which assist the microprocessor 136 in controlling the system of the present invention (see more detailed discussion below, with reference to FIG. 9). The second microprocessor interface unit 140 also provides control inputs to the microprocessor 136, and includes circuitry to determine the location of the holes in the chart paper of the chart recorder 62 so as to accomplish the auto-index function (also discussed in more detail below, with reference to FIG. 10). A character generator 142 is connected to microprocessor 136 to permit the chart recorder 62 to print alphanumeric characters. Character generator 142 is discussed in more detail below, with reference to FIG. 11.

FIG. 4A is a detailed block diagram of a portion 122' of the program monitor group select 122 of FIG. 3, while FIG. 4B contains a series of tables describing logic operations to be performed by logic unit 154 contained in the portion 122' of FIG. 4A. It isto be noted that program monitor group select 122 contains not only portion 122' (which suffices for Monitor Group I), but also additional elements for selection of Monitor Groups II and III. Referring to FIG. 4A, the portion 122' comprises encoder 150, magnitude comparator 152 and logic unit 154. As previously discussed with respect to the control console of FIG. 1, the operator can operate a monitor switch 48 so as to designate a monitor group of lead data which will be recorded and displayed on designated channels of the scope 40 and chart 64. In addition, the operator can operate rotary switches 50, 52 and 54 (designated the Group I, Group II, and Group III selection switches, respectively) to select the three leads to be included in the special monitor group. Furthermore, the operation, by operation of selected switches 56, 58 and 60, can choose the particular channel of the scope 40 and chart recorder 62 on which data from the respective first, second, and third special monitor group leads will be recorded.

Referring to FIG. 4A, encoder 150 receives the Group I selection switch designator from the rotary switch 50, and encodes that designator to develop a three-bit monitor lead code output for Group I. It is to be understood that the program monitor group select 122 contains two further encoders (identical to encoder 150) for generating the monitor lead code outputs for Groups II and III, respectively, but such encoders have been deleted from FIG. 4A for the sake of simplicity.

The portion 122' includes a magnitude comparator 152 which receives output channel designations CH1, CH2 and CH3 from the Group I selector switch 56, and further output channel designations CH1', CH2' and CH3' from the Group II selector switch 58. Although not shown for the sake of simplicity, it is to be understood that the program monitor group select 122 also includes further comparators (identical to magnitude comparator 152) for receiving output channel designations from Group II and Group III selection switches 58 and 60, respectively, and from Group III and Group I selection switches 60 and 56, respectively. Further referring to FIG. 4A, the magnitude comparator 152 checks the respective channel inputs for Groups I and II, and generates an output $G1=G2$ when identical channel selection inputs are present. Corresponding magnitude comparators (not shown in FIG. 4A) identical to magnitude comparator 152 generate outputs $G1=G3$ and $G2=G3$.

As previously stated, rotary switches 50, 52 and 54 are provided with a "null" position, by means of which the operator can elect not to choose a given lead on any of Group I, II and III selection switches 50, 52 and 54. In addition, as previously stated, the designation of identical output channels for two or more groups (by identical setting of two or more of switches 56, 58 and 60) will effectively result in a "null" operation with respect to the "special program monitor group selection" feature. This "nulling" operation is accomplished via OR gate 156, which receives the NULL input from the Group I selection switch 50, as well as the $G1=G2$ output of the magnitude comparator 152, and the $G1=G3$ output from the Group II magnitude comparator (not shown).

The portion 122' of FIG. 4A further comprises logic unit 154 which receives "Channel 2" and "Channel 3" selection inputs from the Group I selection switch 56 (inputs CH2 and CH3), Group II selection switch 58 (CH2' and CH3') and Group III selection switch 60 (CH2" and CH3"). Logic 154 also receives the $G1=G2$ output of magnitude comparator 152, as well as the outputs $G1=G3$ and $G2=G3$ from the Group II and Group III magnitude comparators (not shown). Finally, logic unit 154 receives an OVERRIDE input from AND gate 158, the latter detecting simultaneous occurrence of outputs $G1=G2$, $G2=G3$ and $G1=G3$ (that is simultaneous occurrence of all channel selection switches 56, 58 and 60 being identically set).

Logic 154 operates in accordance with the operations indicated by the tables of FIG. 4B, so as to generate monitor group channel codes for each channel (A3, A4 for channel 1; B3, B4 for channel 2; and C3, C4 for channel 3). That is to say, logic unit 154 responds to the channel selection inputs CH2, CH3, etc., and to the magnitude comparator outputs G1=G2, G1=G3 and G2=G3, to determine which particular group has been assigned to channels 1, 2 and 3, respectively, and provides a two-bit output A3, A4 comprising a channel code for Monitor Group I, a two-bit output B3, B4 comprising a channel code for Monitor Group II, and a two-bit output C3, C4 comprising a channel code for Monitor Group III. The output channel codes and the various channels indicated by those codes are set forth in FIG. 4B. Moreover, logic unit 154, in response to input OVERRIDE from AND gate 158, provides a special override channel code indicated in FIG. 4B.

Figure 5A:
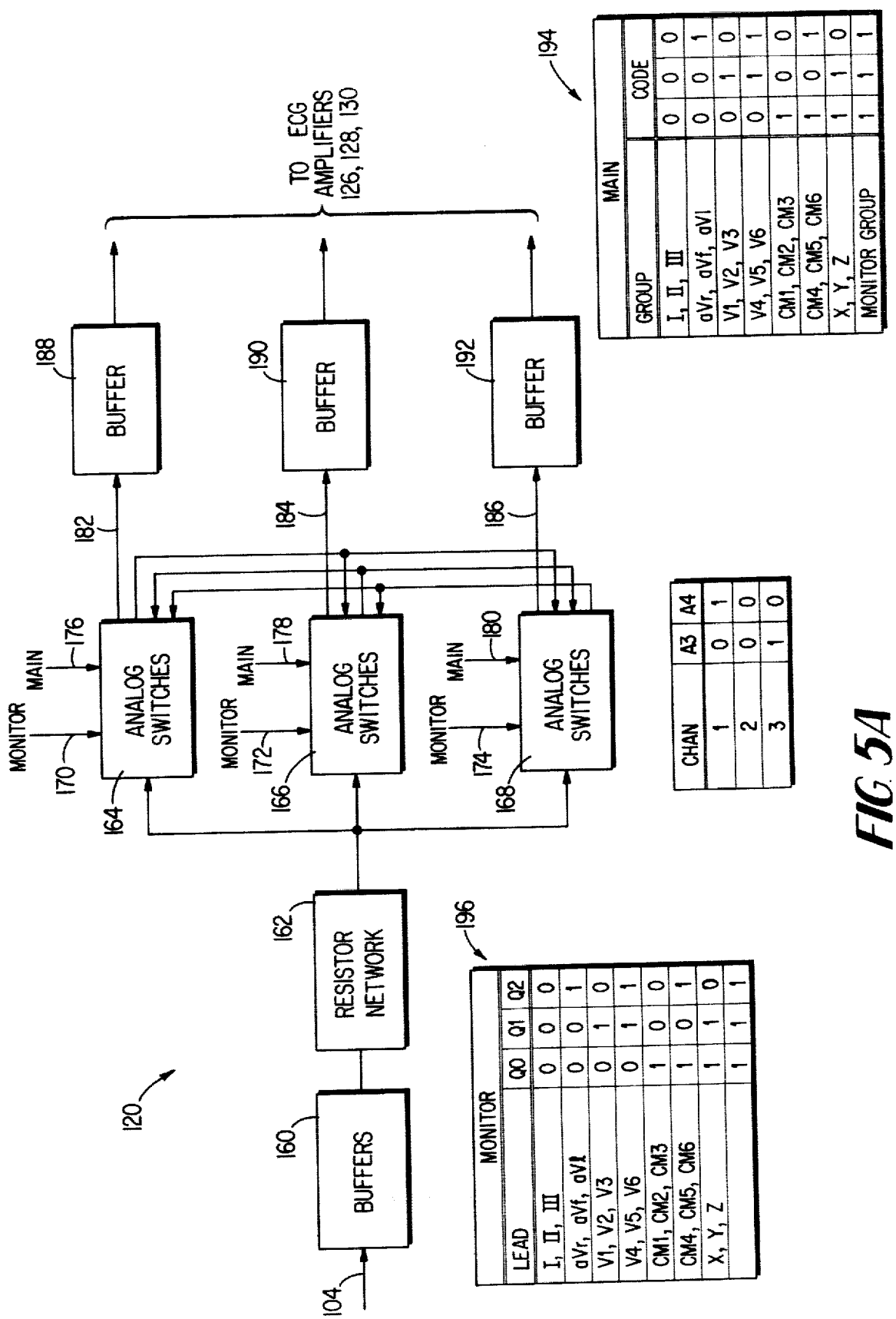
FIG. 5A is a more detailed block diagram of the lead switching unit 120 of FIG. 3.

FIG. 5A is a more detailed block diagram of the lead switching unit 120 of FIG. 3. As seen therein, the lead switching 120 comprises buffers 160, resistor network 162, analog switches 164, 166 and 168, and output buffers 188, 190 and 192. In operation, the lead switching unit 120 receives the ECG signals on pickup leads 104. The leads 104 are connected to buffers 160 which are conventional buffer amplifiers (set for a unity gain). After buffering therein, the ECG signals are provided to resistor network 162 which serves to develop the buffered ECG signals into standard ECG lead data inputs. More specifically, in the preferred embodiment, there are thirteen pickup leads, a fourteenth lead being connected to the right leg of the patient and to system ground.

Figure 5B:
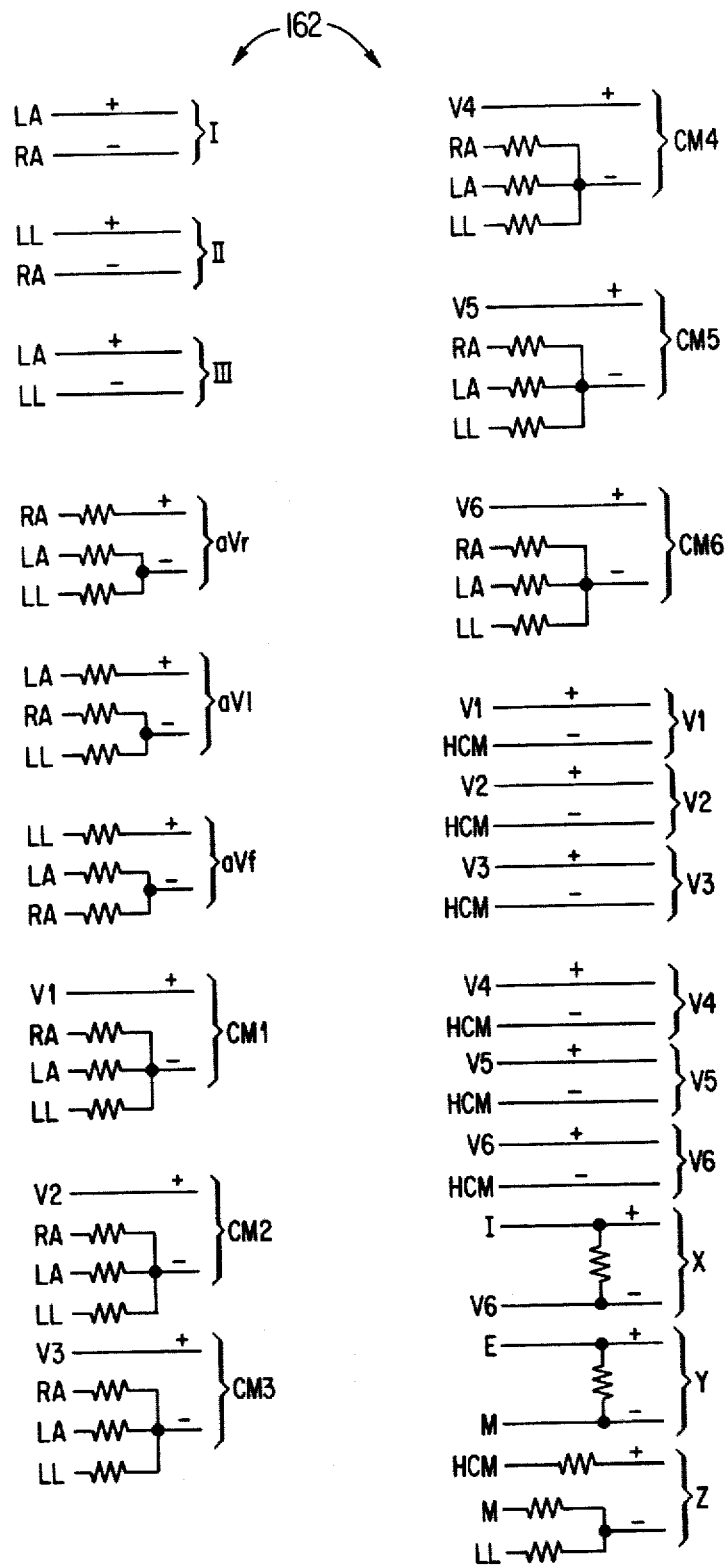
FIG. 5B is a detailed schematic of the resistor network 162 of FIG. 5A.

As shown in detail in FIG. 5B, the resistor network 162 receives the thirteen input signals (I, E, M, HCM, V1, V2, V3, V4, V5, V6, RA, LA and LL) from the pickup leads, and develops these inputs into twenty-one standard ECG lead data inputs (I, II, III, aVr, aVl, aVf, CM1, CM2, CM3, CM4, CM5, CM6, V1, V2, V3, V4, V5, V6, X, Y and Z). It is to be understood that the resistor network 162 could be configured in any other manner, obvious to one of skill in the art of electrocardiographic testing, without departing from the spirit and scope of this invention.

Returning to FIG. 5A, analog switches 164, 166 and 168 are essentially a plurality of field-effect transistors, each of which receives seven of the twenty-one standard ECG data inputs. That is to say, analog switch 164 receives inputs I, aVr, etc.; analog switch 166 receives inputs II, aVl, etc.; and analog switch 168 receives inputs III, aVf, etc. In response to input MAIN (a three-bit input from the microprocessor interface unit 140 of FIG. 3), analog switches 164, 166 and 168 determine whether or not one of the standard lead groups has been selected by the operator, and, if so, which standard lead group has been selected (see Table 194 of FIG. 5A). In response to a predetermined MAIN input (111), analog switches 164, 166 and 168 determine that the "Special Monitor Group" feature has been selected. In the latter case, analog switches 164, 166 and 168 respond to the respective five-inputs MONITOR provided via lines 170, 172 and 174, respectively, to determine which leads have been selected by the operator for inclusion in the Special Monitor Group, and also to determine which channel has been selected by the operator for each of the selected leads. More specifically, analog switch 164 responds to the monitor lead code for Group I (Q0, Q1, Q2) generated by encoder 150 (FIG. 4A) to select one of the leads I, aVr, etc.; analog switch 166 responds to the monitor lead code for Group II generated by a corresponding encoder (not shown) in the program Monitor Group select 122 (FIG. 3) to select one of the leads II, aVf, etc.; and analog switch 168 responds to the monitor lead code for Group III to select one of the leads III, aVl, etc. In addition, analog switch 164 responds to the channel code for Monitor Group I (A3, A4) generated by the logic unit 154 (FIG. 4A) to determine the particular channel to which the selected lead is to be provided. For example, if lead I is selected for channel 2, analog switch 164 selects lead I and provides the data therefrom, via analog switch 2, to channel 2 (specifically to buffer 190).

In the latter manner the outputs of the analog switches 164, 166 and 168 are provided on lines 182, 184, and 186, respectively. The signals are then buffered in buffer amplifiers 188, 190 and 192, respectively, and are then provided to respective ECG amplifiers 126, 128 and 130 (FIG. 3).

Figure 6:
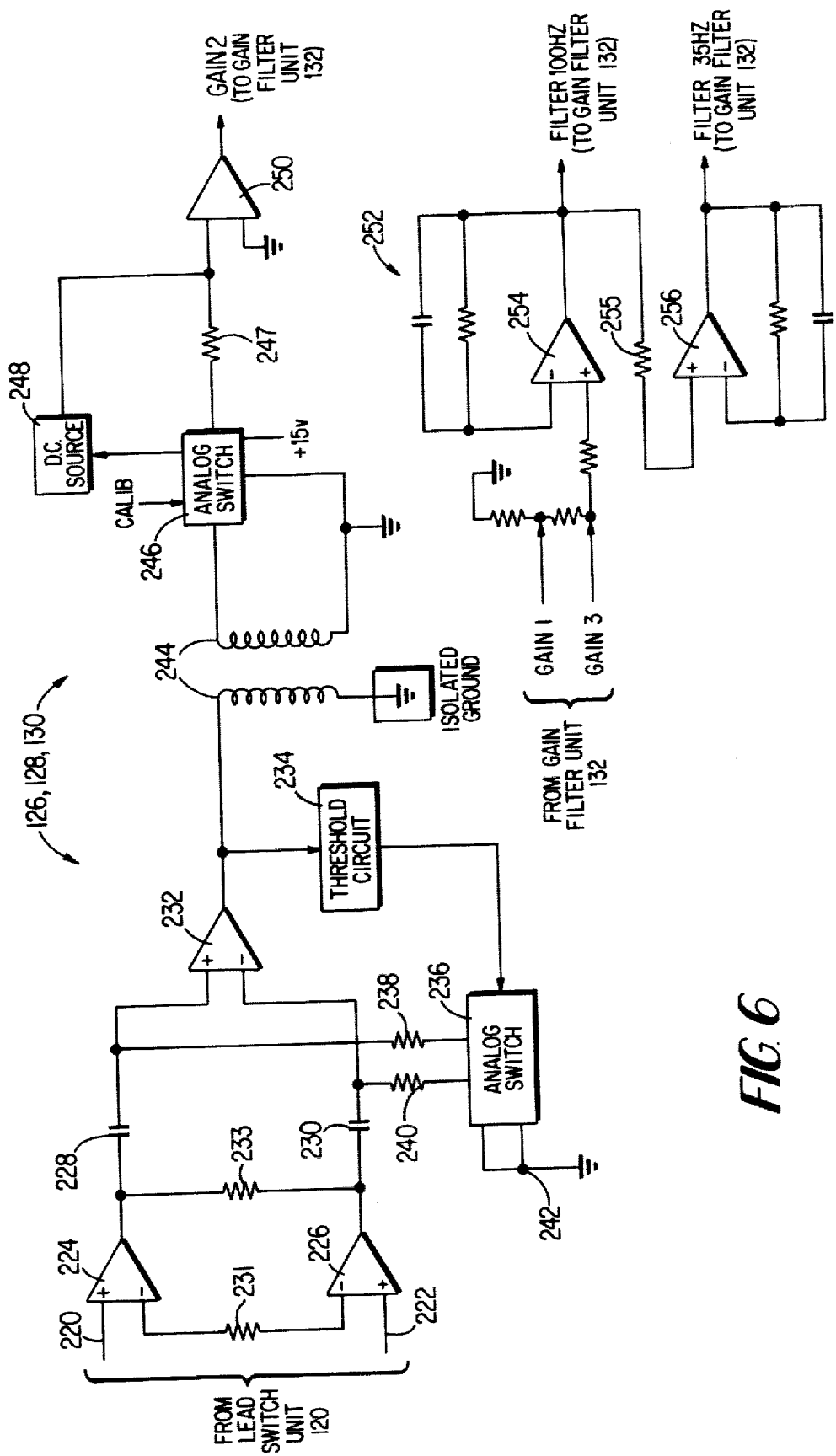
FIG. 6 is a schematic diagram of each amplifier 126, 128 and 130 of FIG. 3.

FIG. 6 is a schematic diagram of each ECG amplifier 126, 128 and 130 of FIG. 3. Each ECG amplifier 126, 128 and 130 is seen to comprise amplifiers 224 and 226, capacitors 228 and 230, differential amplifier 232, threshold circuit 234, analog switch 236, resistors 238 and 240, and ground connection 242, as well as transformer 244, analog switch 246, DC source 248, and amplifier 250. Moreover, each ECG amplifier 126, 128 and 130 comprises a further portion 252 including differential amplifiers 254 and 256, and associated resistors and capacitors (as shown).

In operation, the selected ECG input data for a given channel is provided by lead switching unit 120 (FIG. 3), via inputs 220 and 222 (FIG. 6), to the positive input terminals of amplifiers 224 and 226, respectively. The output signals of amplifiers 224 and 226 are then provided, via capacitors 228 and 230, respectively, to the positive and negative inputs, respectively, of amplifier 232. Capacitors 228 and 230 are preferably of large capacitance (on the order of 40 mf.), and have their input sides connected in common resistor 233; this serves to prevent occurrence of discontinuities in the outputs of amplifiers 224 and 226, when the leads are switched, by storing the voltage of the amplifier output signals, and then supplying such stored voltage signals when the leads are disconnected from the amplifier. It has been found that use of such large capacitances, while preferably from the latter standpoint, causes overloading of the output differential amplifier 232 when a previous low signal is discontinued. As a result, a higher voltage signal is provided from the lead switching unit 120 (FIG. 3) since the capacitors 228 and 230 are already fully charged. Thus, the capacitors 228 and 230 are unable to absorb any additional voltage, and the amplifier 232 tends to overload and distort the output of the ECG amplifier 126, 128, 130.

To eliminate this problem, the system of the present invention employs a threshold circuit 234 connected to the output of the main differential amplifier 232. Threshold circuit 234 senses the overloading of the amplifier 232 in relation to a preset threshold, and provides a control signal to an analog switch unit 236, causing analog switch 236 to connect the capacitors 228 and 230 to ground via respective load resistors 238 and 240 and ground connection 242. Thus, the ECG amplifiers 126, 128, 130 of FIG. 5 operate in such a manner that, during the normal course of amplification, the capacitors 228 and 230 are charged to their maximum capacity. When the input from lead switching unit 120 of FIG. 3 changes, such that the capacitors can no longer absorb overvoltages, and such that the output of amplifier 232 begins to saturate or overload, the threshold circuit 234 senses such overload and provides control signal 236 to the analog switch 238 so as to connect the outputs of the capacitors 228 and 230 to ground, thereby diminishing the overload condition at the input of amplifier 232. The threshold circuit 234 will cease providing the control signals when the output of amplifier 232 is no longer overloaded, and the capacitors 228 and 230 will be disconnected from ground by analog switch 238.

Further considering the operation of ECG amplifiers 126, 128 130, the output of differential amplifier 232 is provided, via transformer 244, to an analog switch 246 which, when in its "closed" position, provides an output signal, via resistor 247, to amplifier 250, the output of which is GAIN2, providing to the gain filters 132 (FIG. 3). Analog switch 246 responds to a control signal input CALIB, provided by gain filters 132, to block passage of the output of amplifier 232 (provided via transformer 244), and instead selects a +15 volt input which is provided to a DC source 248. In response thereto, the DC source 248 generates a reference signal corresponding to the input of one millivolt at the electrode leads connected to the patient, and provides the generated reference signal, via amplifier 250, as output GAIN2 to the gain filter unit 132 (FIG. 3). As will be explained further below, this results in provision of a calibration signal on the given channel, which calibration signal is recorded on chart recorder 62 for the convenience of the attending physician or test administrator.

Figure 7A:
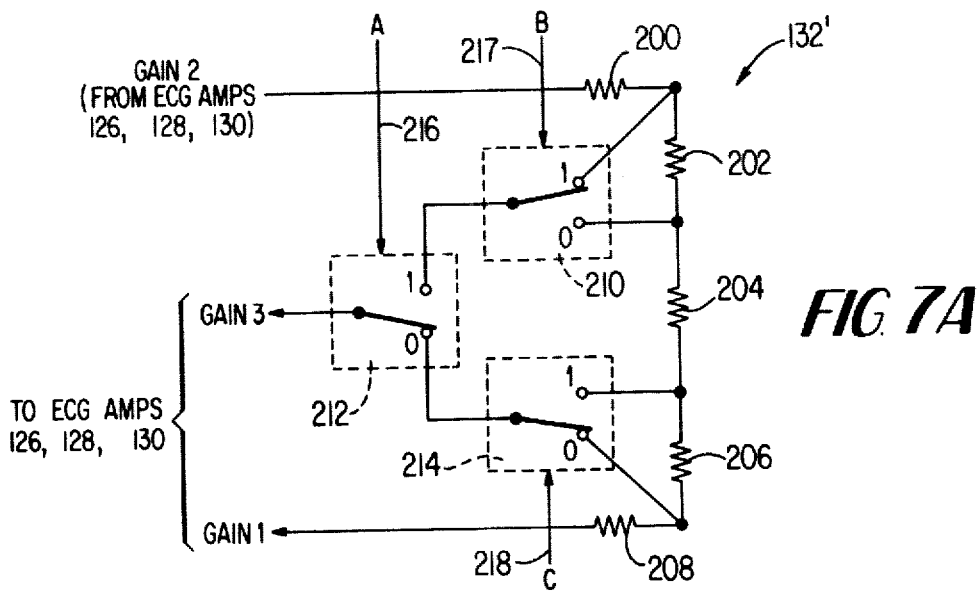
FIGS. 7A, 7B, 7C and 7E are diagrams of the gain filter unit 132 of FIG. 3.
Figure 7B:
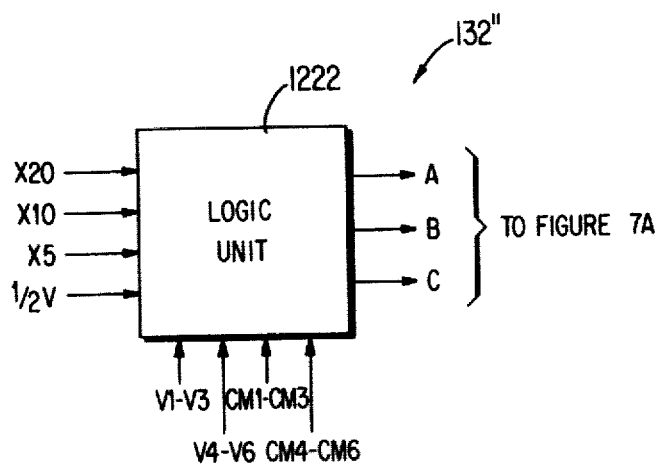
Figure 7C:
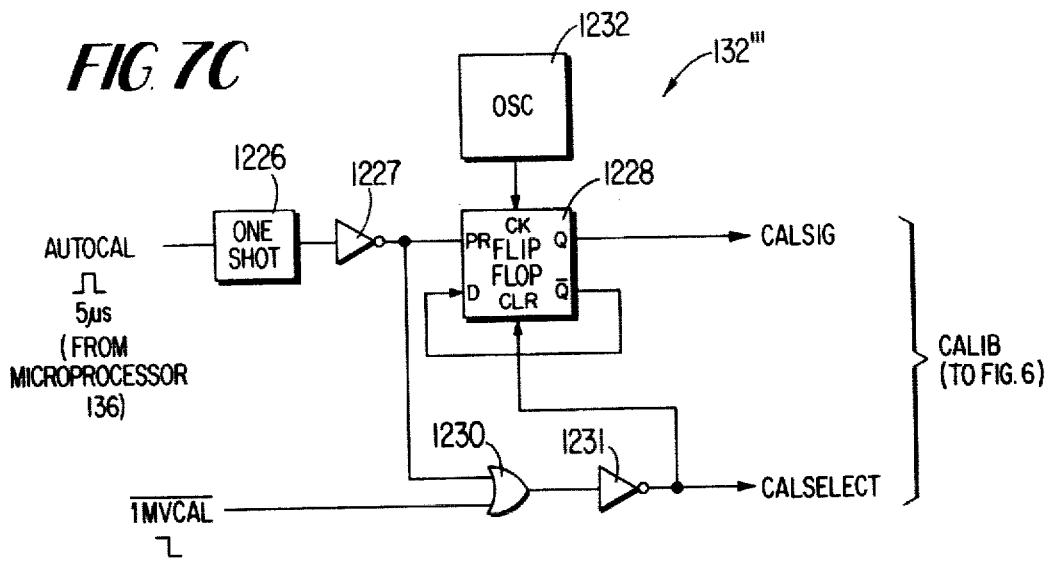
Figure 7D:
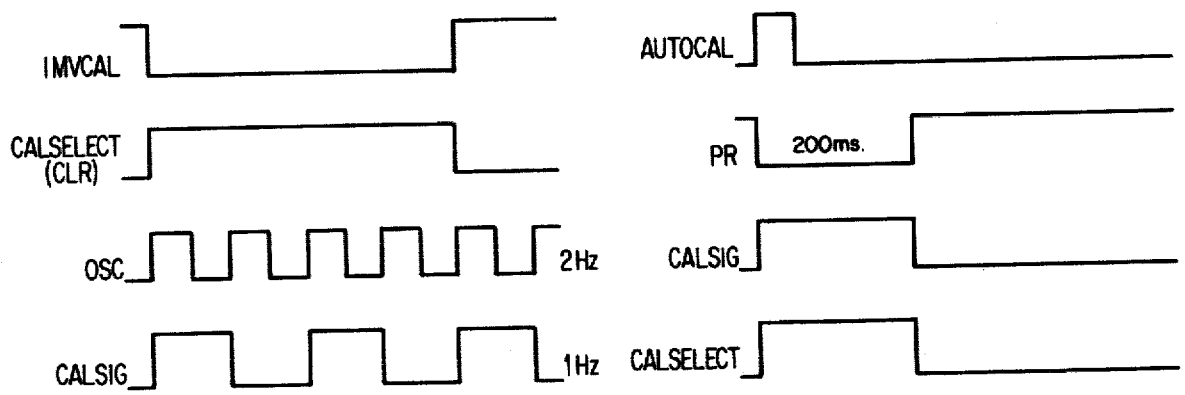
FIG. 7D is a timing diagram describing the operation of the circuit of FIG. 7C.

FIGS. 7A, 7B, 7C and 7E are diagrams of the gain filter unit 132 of FIG. 3, while FIG. 7D is a timing diagram relating to the operation of the gain filter unit 132 of FIG. 3.

As previously discussed in relation to the control console (FIG. 1) of the present invention, a sensitivity switch 18 permits the operator to select the tracing sensitivity (5, 10 or 20 millimeters per millivolt) of the chart recorder 62. Additionally, a switch 20 permits the operator to reduce the amplitudes of the precordial lead tracings by one-half. The gain filter unit 132 accomplishes the latter functions.

Specifically, referring to FIG. 7A, the unit 132 includes a resistor network 132' for each channel, such resistor network including five resistors 200, 202, 204, 206 and 208, and three double-pole, double-throw switches 210, 212 and 214 which are under the control of the control console switch 18. The resistor network 200, 202, 204, 206 and 208, together with the switches 210, 212 and 214, acts like a potentiometer with four discrete positions. Although the aforementioned switches are shown in the circuit of FIG. 7A as being mechanically actuated switches, they may actually be analog switches or transistor switches controlled by the electrical control signals A, B and C provided on lines 216, 217 and 218, respectively. The control signals (A,B,C) on lines 216, 217 and 218 are derived from the sensitivity switch 18 on the control console of FIG. 1, as will be discussed in more detail below. In this manner, the various sensitivities may be obtained in accordance with the setting of the switches 210, 212 and 214.

As mentioned with respect to FIG. 6, the output GAIN2 of ECG amplifiers 126, 128, 130 (specifically, the output of amplifier 250 in each ECG amplifier) is provided to the gain filter unit 132, and specifically to the portion 132' shown in FIG. 7A. Control inputs A, B, C are a three-bit input code derived from the settings of the sensitivity switch 18 and ½-amplitude switch 20 on the control console 108 (FIG. 3).

More specifically, as shown in FIG. 7B, gain filter units 132 include a portion 132", basically comprising a logic unit 1222 operating in accordance with the logic diagram 1224 of FIG. 7B. Logic unit 1222, operating in accordance with the diagram 1224, receives and processes sensitivity inputs X5, X10 and X20 (indicating selection of 5, 10 or 20 millimeters per millivolt sensitivity, respectively) from the switch 18, and also receives and processes input ½ V (the ½-amplitude input) from the switch 20. Moreover, logic unit 1222 receives and processes inputs V1-V3, V4-V6, CM1-CM3, CM4-CM6 (indicating operator selection of one of these standard lead groups) from the microprocessor interface unit 140 (FIG. 3). The four inputs from the microprocessor interface unit 140 are "active low" signals which enable the ½ V input to the logic unit 1222. That is to say, when data from one of the chest lead groups V1-V3, V4-V6, CM1-CM3, or CM4-CM6 is being displayed, then the logic unit 1222 will enable the ½ V input thereto (the latter indicating selection, by the operator, of the ½-amplitude feature). Logic unit 1222 will then, in accordance with the logic table 1224, provide outputs A, B, C of the designated type in response to the settings of the calibration switch 18 (having outputs X20, X10 and X5) and the ½-amplitude switch 20 (with output ½ V). Logic unit 1222 provides the three-bit digital control output A, B, C to portion 132' (FIG. 7A) so as to appropriately set switches 212, 210 and 214, respectively (in accordance with the "0" and "1" positions thereof). Respective settings of the switches 210, 212, and 214 result in respective amplification of the GAIN2 input, resulting in an amplified output provided on output lines GAIN3 and GAIN1, this amplified output being provided to the circuitry 252 in ECG amplifiers 126, 128, 130 of FIG. 6.

Figure 7E:
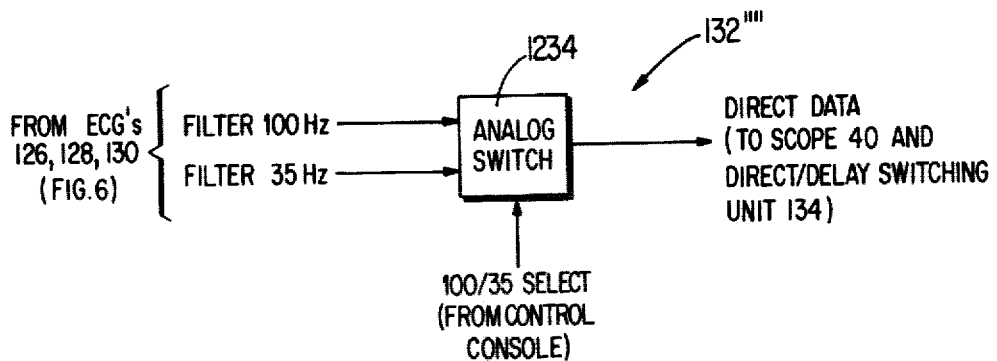

Returning to FIG. 6, circuitry 252 basically comprises differential amplifiers 254 and 256, and associated resistors and capacitors, as shown. Amplified output GAIN3-GAIN1 is provided to the non-inverting input of differential amplifier 254 (via unreferenced input resistors), the inverting input of differential amplifier 254 being connected in feedback arrangement (via a capacitor-resistor network) to the output thereof. Differential amplifier 254 processes this input so as to derive output FILTER100 HZ, a 100-Hertz filtered output provided to the gain filter unit 132 (FIG. 7E). Moreover, the output of differential amplifier 254 is provided, via resistor 255, to the non-inverting input of differential amplifier 256, the inverting input of which is also connected in feedback fashion. Differential amplifier 256 provides further filtering to derive output FILTER3 HZ, a 35-Hertz filtered output provided to the gain filter unit 132 (FIG. 7E).

As mentioned previously, the gain filter unit 132 (FIG. 3) also provides a signal output CALIB to the ECG amplifiers 126, 128, 130, the latter signal CALIB serving to verify the amount of amplification taking place in the amplifiers 126, 128, 130. In actuality, signal CALIB comprises two outputs, CALSIG and CALSELECT, these two signals being produced by further portion 132''' of FIG. 7C.

As seen in FIG. 7C, two control signals, AUTOCAL and 1MVCAL are received by the portion 132'''. AUTOCAL is provided by the microprocessor 136, while input 1MVCAL is provided by the control console switch 22 (designated the "1 mV CAL" calibration switch). Referring to the logic block diagram of FIG. 7C and the timing diagram of FIG. 7D, when the microprocessor 136 generates AUTOCAL (a very short pulse, preferably, 5 microseconds in length), it is received by one-shot device 1226, the latter being activated to the high state for a one-shot duration time of 200 milliseconds. Accordingly, the inverted output of one-shot 1226 (provided by inverter 1227) is a 200-millisecond low input to flip-flop 1228, the input acting as a preset input to the flip-flop 1228. Since the preset line of flip-flop 1228 is an "active low" signal, the inverted one-shot pulse holds the Q output of the flip-flop 1228 high for the length of the one-shot pulse. The Q output of the flip-flop 1228 provides the output CALSIG, forming one of the signals of control output CALIB provided by gain filter 132 to the ECG amplifiers 126, 128, 130. The output of one-shot 1226 is also provided, via inverter 1227, to one input of OR gate 1230, the output of which generates, via inverter 1231, output CALSELECT. The latter forms the second portion of the control output CALIB to the amplifiers 126, 128, 130. Moreover, the output CALSELECT is routed to the clear (CLR) input of flip-flop 1228. The CLR input of flip-flop 1228 is an "active low" input so that, when CALSELECT goes high, the "clear" function of the flip-flop 1228 is disabled temporarily.

In short, generation of the AUTOCAL pulse by the microprocessor 136 results in generation of outputs CALSIG and CALSELECT for the duration of the one-shot 1226. As a result, the ECG amplifiers 126, 128, 130 (FIG. 6) are actuated to provide, by operation of the analog switch 246, DC source 248 and amplifier 250 thereof, an output corresponding to an input of 1 millivolt at the patient leads, this output comprising the GAIN2 output provided to the gain filter unit 132, and constituting a calibration output.

Returning to FIGS. 7C and 7D, the portion 132''' comprises an oscillator 1232 connected to the clock input of flip-flop 1228, the oscillator running at a prescribed rate (for example, 2 Hertz). When the operator depresses the calibration switch 22 on the control console, signal 1MVCAL goes high, resulting in a low input to the OR gate 1230, further resulting in a high output of the inverter 1231, this output forming CALSELECT. The output CALSELECT is applied to the CLR input of flip-flop 1228 (this clear input being, as previously described, an "active low" input), so that the output of oscillator 1232 is permitted to clock the flip-flop 1228. Since the output Q complement is tied to the D input of the flip-flop 1228, the flip-flop 1228 acts as a divide-by-two counter with respect to the 2 Hertz input from the oscillator 1232, resulting in an output CALSIG which oscillates at a rate of 1 Hertz.

Thus, when the operator activates the calibration switch 22, CALSELECT goes high for the duration of the actuation of the calibration switch 22, and output CALSIG is caused to oscillate at a predetermined rate. Referring back to FIG. 6, this causes the ECG amplifiers 126, 128, 130 to periodically generate a 1 millivolt calibration pulse (GAIN2 provided to the gain filter unit 132) as long as the calibration switch 22 is depressed by the operator.

Finally, gain filter unit 132 (specifically, portion 132'''' thereof) provides switching for the FILTER100 HZ and FILTER35 HZ signals from the ECG amplifiers 126, 128, 130. Specifically, these two signals are provided to an analog switch 1234 which responds to a 100/35 SELECT input from the control console (corresponding to actuation of the artifact filter switch 16 to either the 35 Hz or 100 Hz settings) to selectively route one of the two signals to an output DIRECT DATA. The latter output is provided by the gain filter unit 132 to the oscilloscope 40 and the direct/delay switching unit 134 (FIG. 3).

Figure 8:
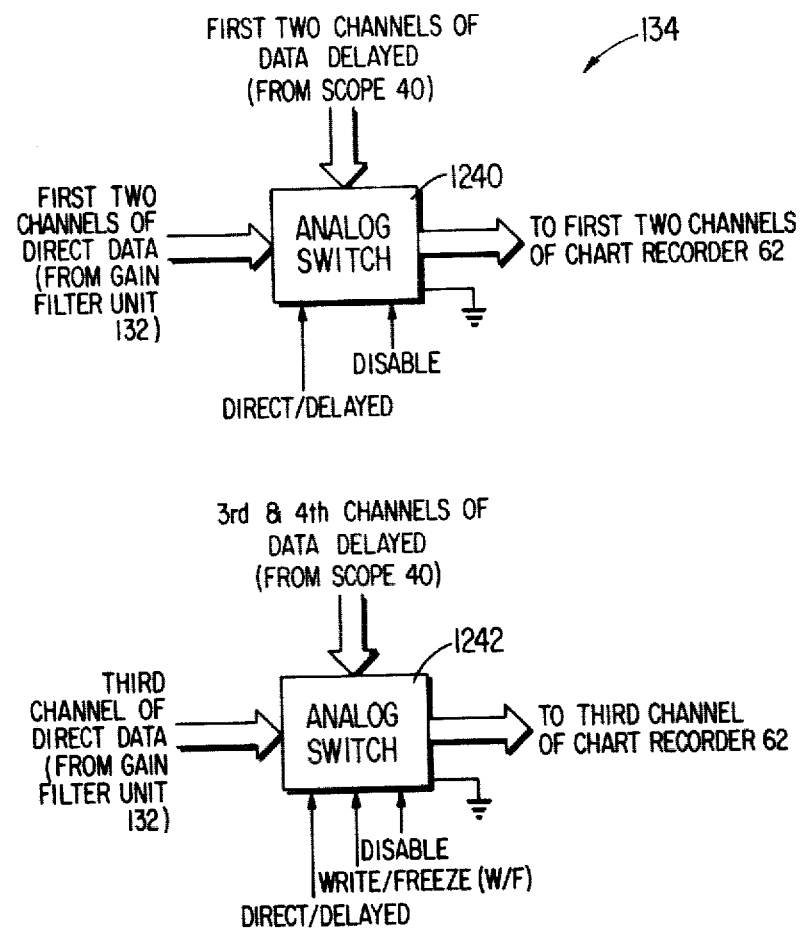
FIG. 8 is a detailed diagram of the direct/delay switching unit 134 of FIG. 3.

FIG. 8 is a detailed diagram of the direct/delay switching unit 134 of FIG. 3. As seen therein, the direct/delay switching unit 134 comprises analog switches 1240 and 1242 which perform functions which will now be described.

In operation, analog switch 1240 receives the first two channels of DIRECT DATA from the gain filter unit 132. Analog switch 1240 also receives the first two channels DATA DELAYED from the oscilloscope 40. In the latter regard, it is to be noted that the data provided directly by the gain filter unit 132 to the oscilloscope 40 is displayed thereon, and, after display (during which a delay is inherently introduced into the data), such data is provided to the direct/delay switching unit 134 as input DATA DELAYED. As previously stated, the control console contains a direct/delayed switch 88 which permits the operator to select (via a "direct" setting) only real-time ECG data for recording on the chart recorder 62. Alternatively, the switch 88 can be actuated (to a "delayed" setting) to cause ECG data previously displayed on the scope (and thus subject to a delay) to be written on the chart recorder 62. The setting of switch 88 is provided to the analog switch 1240 as input DIRECT/DELAYED, in response to which analog switch 1240 selectively chooses the first two channels of DIRECT DATA or the first two channels of DATA DELAYED to be provided as an output to the chart recorder 62. Analog switch 1240 also receives a control input DISABLE, provided by the microprocessor 136 to disable the operation of the direct/delay switching unit 134.

Direct/delay switching unit 134 also comprises analog switch 1242 which receives a third channel of DIRECT DATA from gain filter unit 132 and third and fourth channels of DATA DELAYED from the oscilloscope 40. Analog switch 1242 responds to control inputs DIRECT/DELAYED and WRITE/FREEZE to select either the third channel of DIRECT DATA, the third channel of DATA DELAYED or the fourth channel of DATA DELAYED. The specific conditions under which the respective data are selected for output to the chart recorder 62 are set forth in Table 1244 of FIG. 8.

More specifically, it is to be noted that the analog switch 1242 receives, in addition to the input DIRECT/DELAYED, the further input WRITE/FREEZE, the latter being provided by microprocessor interface unit 140 (FIG. 3) in response to operator actuation of control console switches 108, specifically, the write/freeze switch 86. Thus, in accordance with Table 1244, when switch 88 is set to the "direct" position, and switch 86 is not actuated, analog switch 1242 will provide the third channel of DIRECT DATA to the third channel of the chart recorder 62. When switch 88 is set to the "delayed" position, and switch 86 is not actuated, analog switch 1242 will provide the third channel of DATA DELAYED to the third channel of the chart recorder 62. Finally, when switch 86 is actuated, indicating selection of the "write/freeze" mode of operation, the fourth channel of DATA DELAYED will be provided to the third channel of the chart recorder.

Thus, to summarize, direct/delay switching unit 134 provides the operator with the options of providing data (generated by the gain filter unit 132 (FIG. 3)) to the chart recorder 62 directly, or to the chart recorder 62 in delayed fashion via the oscilloscope 40. Moreover, the operator is provided with the additional capability, via actuation of write/freeze channel switch 86, to provide previously "frozen" data from the fourth channel of the oscilloscope 40 to the third channel of the chart recorder 62.

Figure 9B:
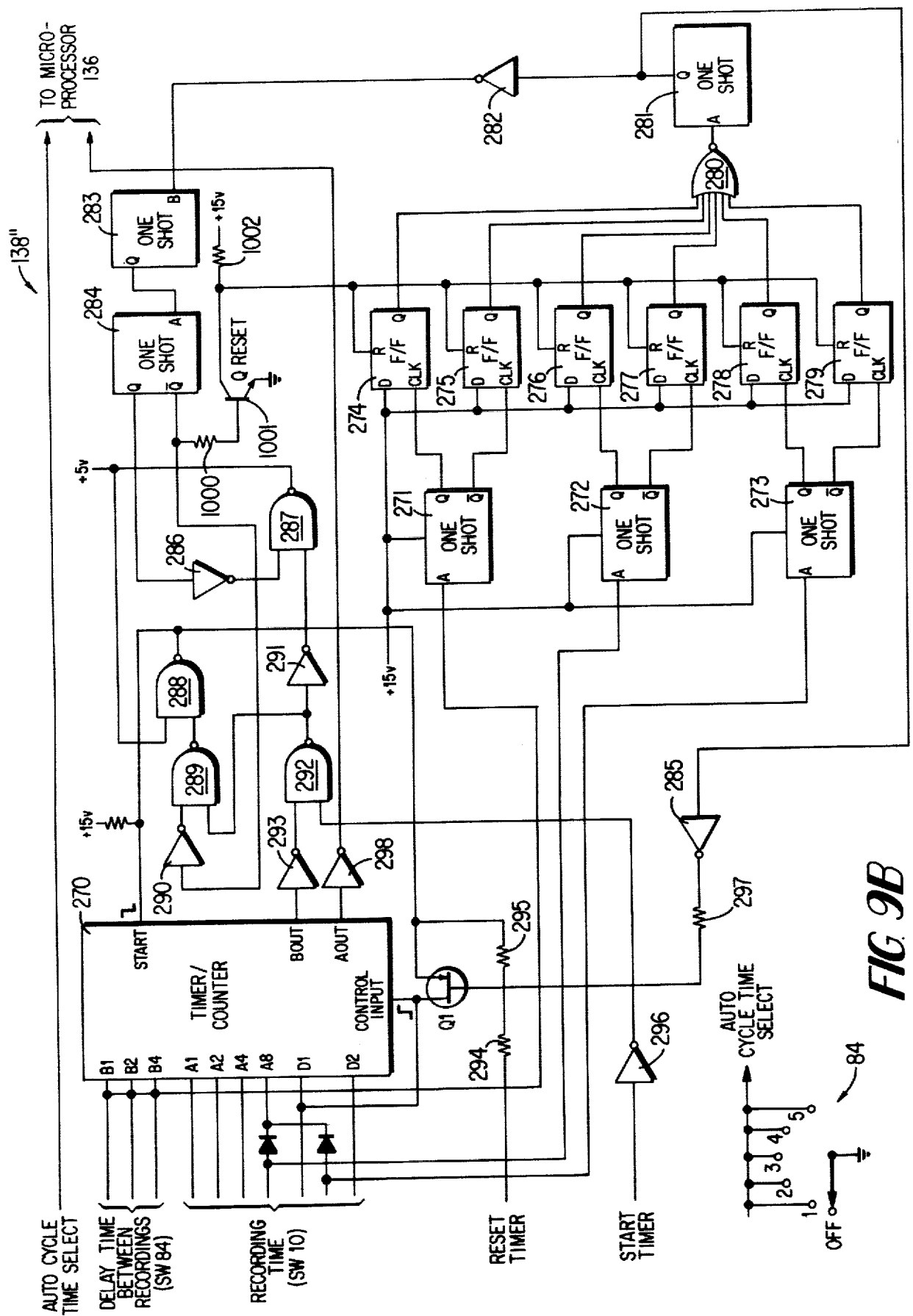

FIGS. 9A and 9B are diagrams of the microprocessor interface unit 138 of FIG. 3. In general, microprocessor interface unit 138 buffers the control console switch signals, and also provides the necessary timing functions for automatic switching features of the system.

Referring to FIG. 9A, a portion 138' of microprocessor interface unit 138 is seen to comprise an encoder 1250, debouncer circuits 1252 through 1262, switches S2 through S10, S11a, S11b, S12a and S12b, and display elements DS11 and DS12. Switches S2 through S9 correspond to control console switches 24, 26, 28, 30, 32, 34, 36 and 38, respectively (FIG. 1). Actuation of one of the latter lead selector switches amounts to closure of a corresponding one of switches S2 through S9, causing an "active low" input to a corresponding one of debouncer circuits 1252 through 1259, the outputs of which are connected to corresponding inputs of encoder 1250. Debouncer circuits 1252 through 1259 are conventional hex switch debouncers which provide clean signals from the noisy contacts of the control console switches.

Priority encoder 1250 responds to the outputs of the debouncer circuits 1252 through 1259 to generate output QS indicating that one of the standard lead groups or the special monitor group has been selected, and output A, B, C comprising a three-bit digital output indicating the particular lead group that has been selected by the operator. The output of encoder 1250 is provided to the processor 136, thus alerting the processor 136 as to the particular lead group selected.

In addition, portion 138' of microprocessor interface unit 138 comprises switch S10 which is closed upon actuation of the auto lead selector switch 12 (FIG. 1), ganged switches S11a and S11b which are closed upon actuation of the auto index switch 90, and ganged switches S12a and S12b which are closed upon actuation of the start chart recorder switch 94 (FIG. 1). Switches S10, S11b and D12b provide respective outputs, via corresponding debouncer circuits 1260 through 1262, to the processor 136. In addition, actuation of the auto index switch 90 and start chart recorder switch 94 causes closure of switches S11a and S12a, respectively, causing application of +5 volts to the display indicators DS11 ad DS12, respectively. In this manner, the operator is alerted in a direct manner, via these control console display indicators, to actuation of the corresponding switches. It is to be noted that selection of the other functions discussed above also results in actuation of display indicators on the control console, but these display indicators are (as will be discussed below) actuated on command of the microprocessor 136, once the microprocessor 136 detects the selection of the given function by means of detection of the outputs of the portion 138' of the microprocessor interface unit 138.

FIG. 9B shows a further portion 138" of the microprocessor interface unit 138 of FIG. 3. In general, the portion 138" of the microprocessor interface unit 138 of FIG. 3 is responsible for implementing the "auto cycle" and "auto lead" features of the present invention. As seen in FIG. 9B, portion 138" generally comprises a timer/counter 270, retriggerable one-shots 27 through 273, flip-flops 274 through 279, NOR gate 280, one-short 281, inverter 282, one-shots 283 and 284, inverter 285, and control input transistor Q1, as well as various other logic elements to be mentioned below.

As mentioned previously, the operator selects and implements the "auto lead" feature of the present system by setting the recording time for each lead group (comprising the leads to be recorded during the "auto lead" operation, as selected by switches 42, 44, 46, and 48) on the thumbwheel switch 10, and by depressing the "auto lead" switch 12 on the control console. This notifies the microprocessor 140 (FIG. 3) that this particular feature has been selected.

Similarly, the operator selects and implements the "auto cycle" feature of the present system by setting a delay time between recordings on rotary switch 84, and setting a recording time on thumbwheel switch 10. Movement of the switch 84 (see FIG. 9B) from the "off" position generates signal AUTO CYCLE TIME SELECT, which is provided by portion 138" to the microprocessor 136 (FIG. 3). Setting of switches 10 and 84 to the recording time and delay time between recordings, respectively, results in setting of the timer/counter 270. The timer/counter 270 is, preferably, a dual set point timer/counter typically utilized for automatic control of interval timing (for example, the DF215 Dual Set Point Timer/Counter, manufactured by Siliconix, Inc). That is, the timer/counter 270 is, preferably, a device containing all necessary logic to implement a dual set point timing or counting scheme, the device typically using two switch banks (such as thumbwheel switch 10 and rotary switch 84 of the present system) to provide two sequential, fully selectable, accurate intervals for equipment control.

More specifically, the timer/coder 270 is of the type which generates two outputs, AOUT and BOUT. When reset, timer/counter 270 generates low AOUT and BOUT outputs. Upon being started, timer/counter 270 generates a high AOUT output until the first set point is reached, after which AOUT goes low, and BOUT goes high. Upon reaching the second set point, BOUT goes low. Moreover, as will be described in more detail below, timer/counter 270 can be so connected as to cause automatic restart of the timer/counter 270 by output BOUT going low (that is, at the end of the second interval). In this manner, "a continuous cycle" mode of operation can be achieved.

Further referring to the portion 138" of FIG. 9B, it is to be noted that, in general, the timer/counter 270 is reset by the occurrence of a low-to-high transition at its control input. Moreover, the timer/counter 270 is started by the occurrence of a high-to-low transition at its START input. Input RESET TIMER (from the microprocessor 136) is normally high, resulting in nonconduction of the transistor Q1, resulting in turn in control of the control input of timer/counter 270 by the digit strobe input D1. When RESET TIMER goes low, transistor Q1 comes on, resulting in application of +15 volts to the control input via the transistor Q1. This resets the timer/counter 270, holding it reset until RESET TIMER goes high. In the reset mode, both AOUT and BOUT are low.

Input START TIMER is a normally high input which, when it goes low, provides a high input to NAND gate 292, resulting in a low input to NAND gate 289, a high input to NAND gate 288, and a high-to-low transition at the START input of timer/counter 270. As will be seen below, inverters 293 and 296, in conjunction with NAND gate 292, perform an OR function between inputs START TIMER and output BOUT of the timer/counter 270. As a result, the timer/counter 270 can be started (or restarted) by either of those two signals.

Moreover, a third means of starting the timer/counter 270 is provided by one-shot devices 283 and 284 operating in conjunction with inverter 286 and NAND gates 287 and 288. This will be discussed in more detail below.

The "auto lead" feature of the present system is implemented in the following manner. As previously mentioned, the operator sets a recording time by means of thumbwheel switch 10, and presses the "auto lead" button 12 on the control console. The processor 136 (FIG. 3) is notified that the "auto lead" feature has been selected, and issues a negative pulse at input RESET TIMER of the portion 138″ (FIG. 9B), the timer/counter 270 being reset via resistor 294 and transistor Q1 connected to the control input of timer/counter 270. At this point, outputs AOUT and BOUT are low.

Microprocessor 136 then starts the timer/counter 270 by generating a negative pulse at START TIMER, resulting (as discussed above) in a high-to-low transition at START. As a result, AOUT goes high, this being detected by microprocessor 136 via inverter 298. During the time AOUT is high, microprocessor 136 causes the chart recorder 62 to record the ECG data from a selected group of the eight lead groups. At the end of the first time interval, as measured by timer/counter 270, output AOUT goes low. Microprocessor 136 detects this condition via inverter 298, and proceeds to select the next lead group from which ECG data is to be recorded. Once the next lead group is selected, the microprocessor 136 rests and restarts the timer-counter 270 in the manner described above.

The "auto cycle" feature of the present system is implemented as follows. As previously discussed, the operator selects the "auto cycle" feature by setting thumbwheel switch 10 and rotary switch 84 to the recording time and time interval between recordings, respectively. Movement of switch 84 from the "off" position to one of the time interval settings causes signal AUTO CYCLE TIMER SELECT to be sent to the microprocessor 136, thus alerting the microprocessor 136 that the "auto cycle" mode has been selected by the operator. Then, upon depression of the start chart recorder switch 94, microprocessor 136 resets the timer/counter 270, via input RESET TIMER, as previously described. The timer/counter 270 is started via input START TIMER, as also previously described. Output AOUT of timer/counter 270 goes high, and the microprocessor 136 detects this condition via inverter 290, and causes the chart recorder 62 to print ECG data from a selected group of leads so long as AOUT remains high. At the end of a recording time, as measured by timer/counter 270, the latter causes AOUT to go low and BOUT to go high. Microprocessor 136 detects this new condition at output AOUT (via inverter 298), and waits for AOUT to go high again. In the meantime, timer/counter 270 measures the delay time between recordings, at the conclusion of which output BOUT goes low. As previously described, when BOUT goes low, this is translated to the START input terminal of timer/counter 270 (via inverter 293 and NAND gates 292, 289 and 288) as a high-to-low transition at that terminal. This causes the timer/counter 270 to restart counting, and output AOUT again goes high. The microprocessor 130 detects this latter condition, and causes the chart recorder 62 to begin recording ECG data from the lead group. Thus, this "auto cycle" mode of operation will continue until the operator cancels his selection (by turning rotary switch 84 to the "off" position).

It is to be noted that a particular feature of the system of the present invention resides in the fact that any alteration, by the operator, of the recording time (as set on switch 10) or the delay time between recordings (as set on rotary switch 84) results in resetting and restart of the timer/counter 270. Specifically, alteration of the aforementioned switches is detected by one of the one-shot devices 271 through 273, with consequent generation of a low-to-high transition at one of the Q or Q complement outputs of a given one of the one-shot devices 271 through 273. This low-to-high transition clocks one of the flip-flop devices 274 through 279, causing a transition to occur at the output of the given flip-flop device. NOR gate 280 performs an OR function with respect to the Q outputs of the flip-flops 274 through 279, so that any alteration of the switches 10 or 84 results in an input to the one-shot device 281, the latter generating an output pulse which is inverted by inverter 285 and provided, via resistor 297, to the base of transistor Q1. As previously described, the latter is caused to conduct, resulting in resetting of the timer/counter 270 via its control input.

In addition, the output pulse of one-shot 281 is inverted by inverter 282, and provided to further one-shot device 283 so as to cause it to provide an output pulse (preferably, of longer duration than the output pulse of one-shot 281) to the A input of one-shot 284. One-shot 284 responds to the Q output pulse of one-shot 283 by generating positive and negative output pulses at the Q and Q complement outputs, respectively, thereof. The Q output is provided via inverter 286 to one input of NAND gate 287 which, via NAND gate 288, causes a high-to-low transition at the START input of timer/counter 270, thus restarting the timer/counter 270. It is to be noted that this resetting and restarting of the timer/counter 270 by alteration of either of switches 10 or 84 is accomplished without regard to the particular mode of operation ("auto lead"0 or "auto cycle") of the system. The Q complement output of one shot 284 is also provided, via resistor 1000, to transistor 1001 (Q RESET), which provides a positive one-shot pulse to the respective reset inputs of flip-flops 274 through 279.

Figure 10A:
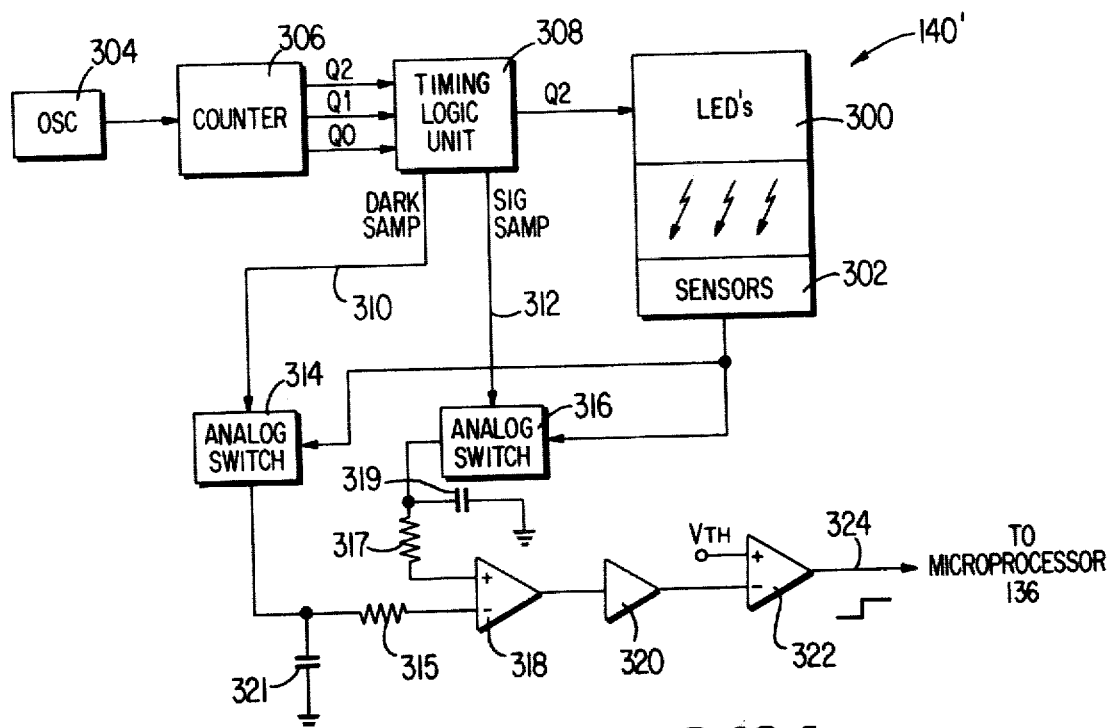

FIGS. 10A through 10D are diagrams of the microprocessor interface unit 140 of FIG. 3, while FIG. 10E is a timing diagram related to FIG. 10A.

As seen in FIG. 10A, microprocessor interface unit 140 includes a portion 140′ which is responsible for accomplishment of the "auto index" feature in accordance with the present invention. The portion 140′ comprises the combination of a light emitting diode (LED) array 300, sensor circuitry 302, oscillator 304, counter 306, timing logic unit 308, analog switches 314 and 316, differential amplifier 318, op amp 320, and further differential amplifier 322.

In operation, oscillator 304 generates a clock output (see FIG. 10E) which is provided to the counter 306. Counter 306 generates successive three-bit counter outputs Q0, Q1 and Q2 (from least significant to most significant bit), and this output is provided to the timing logic unit 308.

Figure 10B:
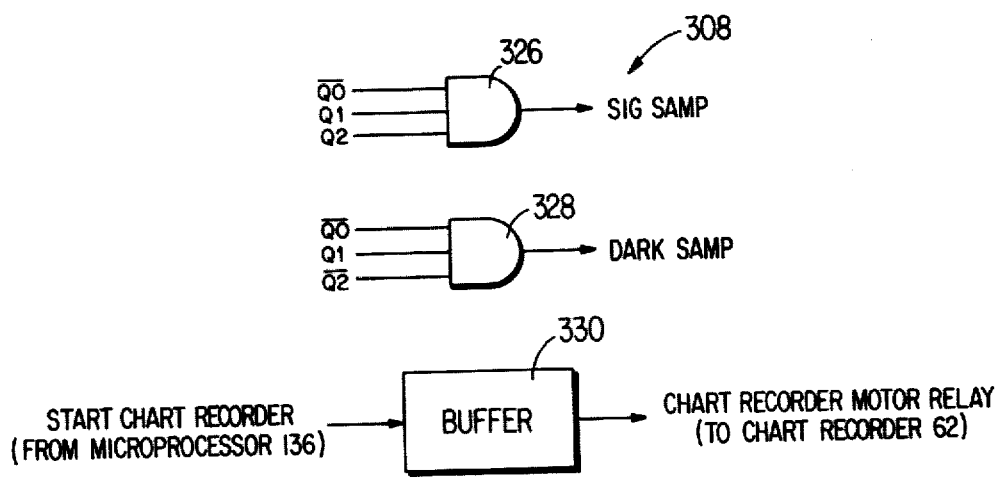

Timing logic unit 308 is shown in more detail in FIG. 10B, and comprises AND gates 326 and 328. As indicated in FIG. 10B, timing logic unit 308 responds to certain three-bit counter outputs to selectively generate outputs DARK SAMP and SIG SAMP, the former signal being provided via output 310 to analog switch 314 (FIG. 10A), the latter being provided via output 312 to analog switch 316.

Timing logic unit 308 also provides output Q2 (the most significant bit of counter 306) to the LED 300 as a driving signal. Thus, it can be seen from FIG. 10E that output SIG SAMP is generated by timing logic unit 308 in the middle of that time interval during which the LED 300 is being driven by signal Q2, while DARD SAMP is generated during that interval when the LED 300 is not being subjected to driving signal Q2. It should be further noted that analog switches 314 and 316 receive the signals DARD SAMP and SIG SAMP via lines 310 and 312, respectively, from the timing logic unit 308, such signals serving as enabling signals for the analog switches 314 and 316, respectively. Thus, during the period when the LED 300 is not being driven, that is, during that time when sensor circuitry 302 is emitting a true "dark" (zero voltage) output, analog switch 314 is enabled to provide this output via sample-and-hold resistor 315 and capacitor 321 to the inverting input of differential amplifier 318. Correspondingly, during the time interval when the LED 300 is being driven by signal Q2, the output from sensor circuitry 302 is provided via line 320, analog switch 316, and sample-and-hold resistor 317 and capacitor 319, to the non-inverting input of differential amplifier 318. When paper is intervening between the LED 300 and the sensor 302, light reflected from the back of the paper is detected by the sensor 302, resulting in a relatively large output via analog switch 316 to the non-inverting input of differential amplifier 318. This results in a relatively large voltage output from differential amplifier 318 via op amp 320 to the inverting input of differential amplifier 322, the non-inverting input of which is provided with a relatively large (approximately 3 volts) threshold voltage VTH. As a result, the detection of such paper corresponds to a "low" output on line 324 thereof. Conversely, when a hole (in the chart paper) intervenes between the LED 300 and the sensor 302, a relatively low voltage is provided to the non-inverting input of differential amplifier 318, wherein it is compared with the "dark" reference voltage provided by analog switch 314. As a result, differential amplifier 318 generates a very small (in the range of millivolts) output via op amp 320 to the inverting input of 322, the output 324 of which goes high, signifying detection of a hole in the chart paper. This "high" signal output is provided to the microprocessor 136 to stop the chart recorder. In that regard, it should be noted that, with reference to FIG. 10B, the chart recorder is started by a command START CHART RECORDER from the microprocessor 136 provided to buffer 330, which provides an output CHART RECORDER MOTOR RELAY to the chart recorder 62.

Microprocessor interface unit 140 contains a further portion 140" shown in FIG. 10C. The portion 140" comprises decoder 332 and driver circuits 334a thru 334h.

In operation, portion 140" receives inputs LEAD GROUP2, 1 and 0 from the microprocessor 136, this signal controlling the lead group from which data is to be recorded by the system. Accordingly, inputs LEAD GROUP2, LEAD GROUP1 and LEAD GROUP0 are inverted by inverters 337 through 339, respectively, providing the complement signals as outputs to the isolators 124 (FIG. 3), such outputs being provided (as previously discussed) to the lead switching unit 120.

Inputs LEAD GROUP2, LEAD GROUP1 and LEAD GROUP0 are further provided to decoder 332, which generates eight outputs corresponding to the particular lead group designated by the three-bit code received from the microprocessor 136. These eight output signals are provided to respective driver circuits (only drivers 334a and 334h are shown for the sake of brevity), with the result that driver signals are generated to activate respective control console lamps corresponding to the particular lead group selected by the operator. Moreover, those output signals, from the decoder 332, which correspond to the selection of the V1-V3, V4-V6, CM1-CM3 and CM4-CM6 groups, are tapped to provide further output signals to the gain filters 132 (FIG. 7B) for the purposes previously discussed above with respect to gain filters 132.

Finally, portion 140" receives inputs AUTO LEAD LAMP and AUTO LEAD LAMP FLASH from the microprocessor 136, these signals being provided to AND gate 340, the output of which provides an enable input to an oscillator 342 which clocks a driver circuit 340 to provide a pulsating driving signal to the console lamp corresponding to the "auto lead" function. This arrangement implements the feature of the present system, whereby, when the "auto cycle" feature is selected by the operator, this condition is detected by the microprocessor 136 (FIG. 3), the latter generating the aforementioned control inputs to portion 140". As a result, so long as the "auto cycle" feature is selected by the operator, the "auto lead" feature is disabled, this being indicated to the operator by a flashing of the "auto lead" console lamp.

Conversely, when the microprocessor 136 indicates that "auto lead" has been selected (by input AUTO LEAD LAMP being high), the output AUTO LEAD LAMP FLASH of microprocessor 136 will be kept low, the latter signal being provided via inverter 346 to AND gate 348, the other input of which receives the AUTO LEAD LAMP input. As a result, AND gate 348 will enable driver 344 to maintain the "auto lead" console lamp constantly on, indicating selection of the "auto lead" feature.

As shown in FIG. 10D, microprocessor interface unit 140 of FIG. 3 contains a further portion 140"', comprising a NAND gate 1352. The latter receives the WRITE/FREEZE ENABLE input from the microprocessor 136, as well as the WRITE/FREEZE SWITCH input through inverter 1351, from the control console switches 108 (indicating that the "write/freeze" feature has been selected by the operator). As a result, NAND gate 1350 generates an output which is provided to the oscilloscope 40 (via inverter 1353) as output CIRC CHAN 4, causing the latter to recirculate (in a conventional manner) the contents of channel 4, as stored therein, thus implementing the "freeze" feature selected by the operator.

Figure 11:
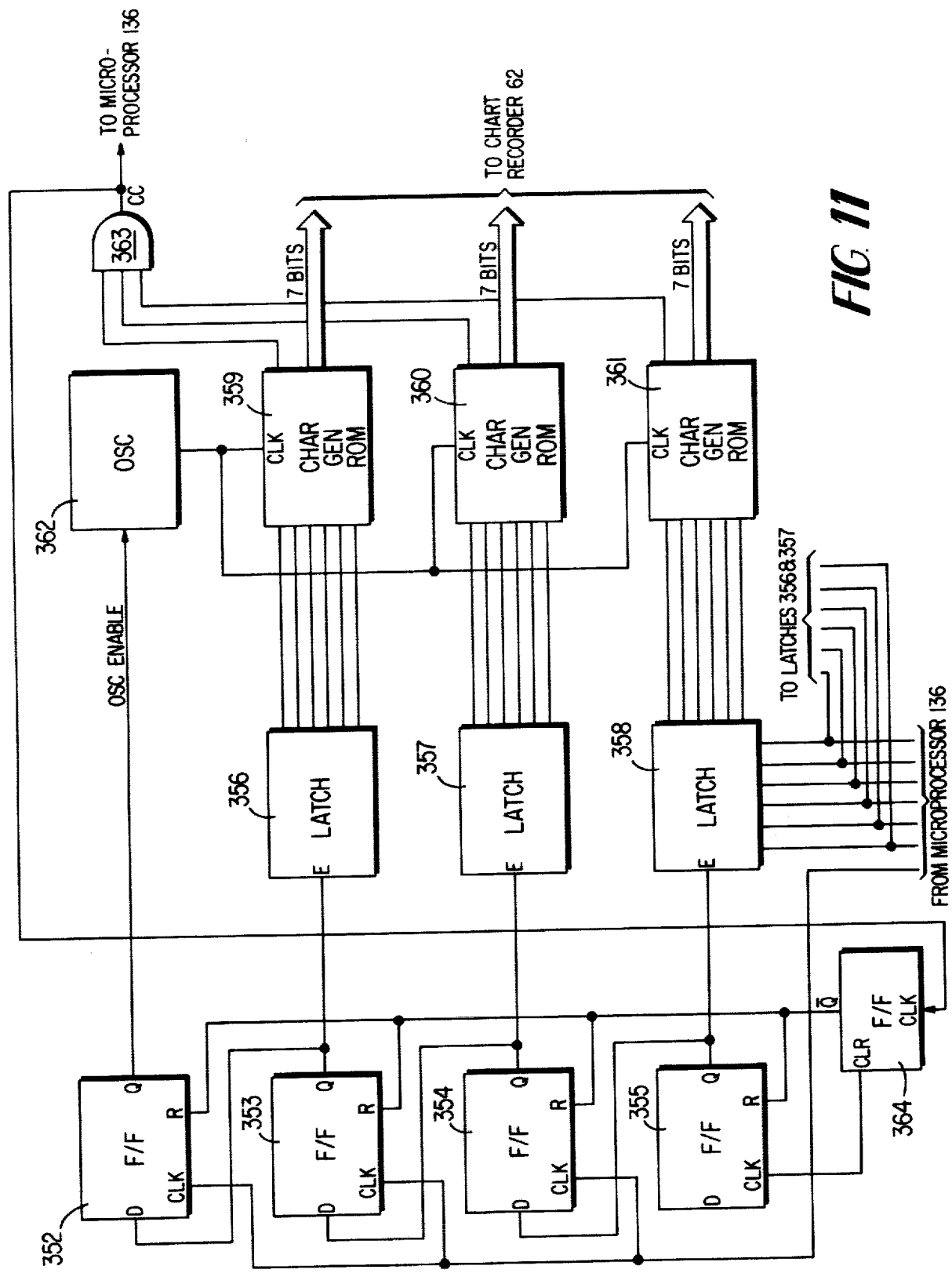
FIG. 11 is a schematic diagram of the character generator unit 142 of FIG. 3.

FIG. 11 is a schematic diagram of the character generator unit 142 of FIG. 3. As seen therein, character generator 142 comprises flip-flops 352 through 355, latches 356 through 358, character generator read-only memories (ROM's) 359 through 361, oscillator 362, AND gate 363 and common reset 364.

In operation, the character generator 142 responds to microprocessor input signals to provide driving signals to the chart recorder 62 for printing, on the chart paper, the identities of the various lead groups for which data is being traced on the chart recorder paper. Specifically, flip-flops 352 through 355 are cleared (via their R inputs) by a signal from the reset flip-flop 364. Flip-flops 352 through 355 are cascade-connected via their respective Q outputs and D inputs (as shown), and each receives (at its CLK input) a clock signal from microprocessor 136. Moreover, the Q output of flip-flop 352 enables an oscillator 362, while the Q outputs of flip-flops 353 through 355 enable latch circuits 356 through 358, respectively.

Latch circuits 356 through 358 perform a latching function with respect to the character code inputs from the microprocessor 136, and provide these character inputs to character generator ROM's 359 through 361, respectively. It should be noted that character codes are provided by the microprocessor 136 in multiplexed fashion on the six input lines, the latter being provided in common to the latch circuits 356 through 358. The latch circuits 356 through 358 are successively enabled by successive Q outputs from the cascade-connected flip-flops 353 through 355; thus, each of latches 356 through 358 is enabled during a particular time slot so as to latch its respective character code from the microprocessor input lines. In this manner, character generator ROM's 359 through 361 receive consecutive inputs from the latches 356 through 358, respectively, and generate consecutive seven-bit outputs, the latter being provided to the chart recorder 62 so as to print consecutive characters in a 5×7 matrix. Upon completion of a character (as detected by the ROM's 359 through 361), the latter generate respective outputs to the AND gate 363, which results in generation of control signal output CC to the microprocessor 136, indicating that a character has been completed. The control signal CC is also provided to reset flip-flop 364 (clock input thereof) and causes flip-flop 364 to generate a clear or reset signal to clear or reset flip-flops 352-355.

FIGS. 12A through 12G are flowcharts of the operations performed by the microprocessor 136 of FIG. 3.

Figure 12A:
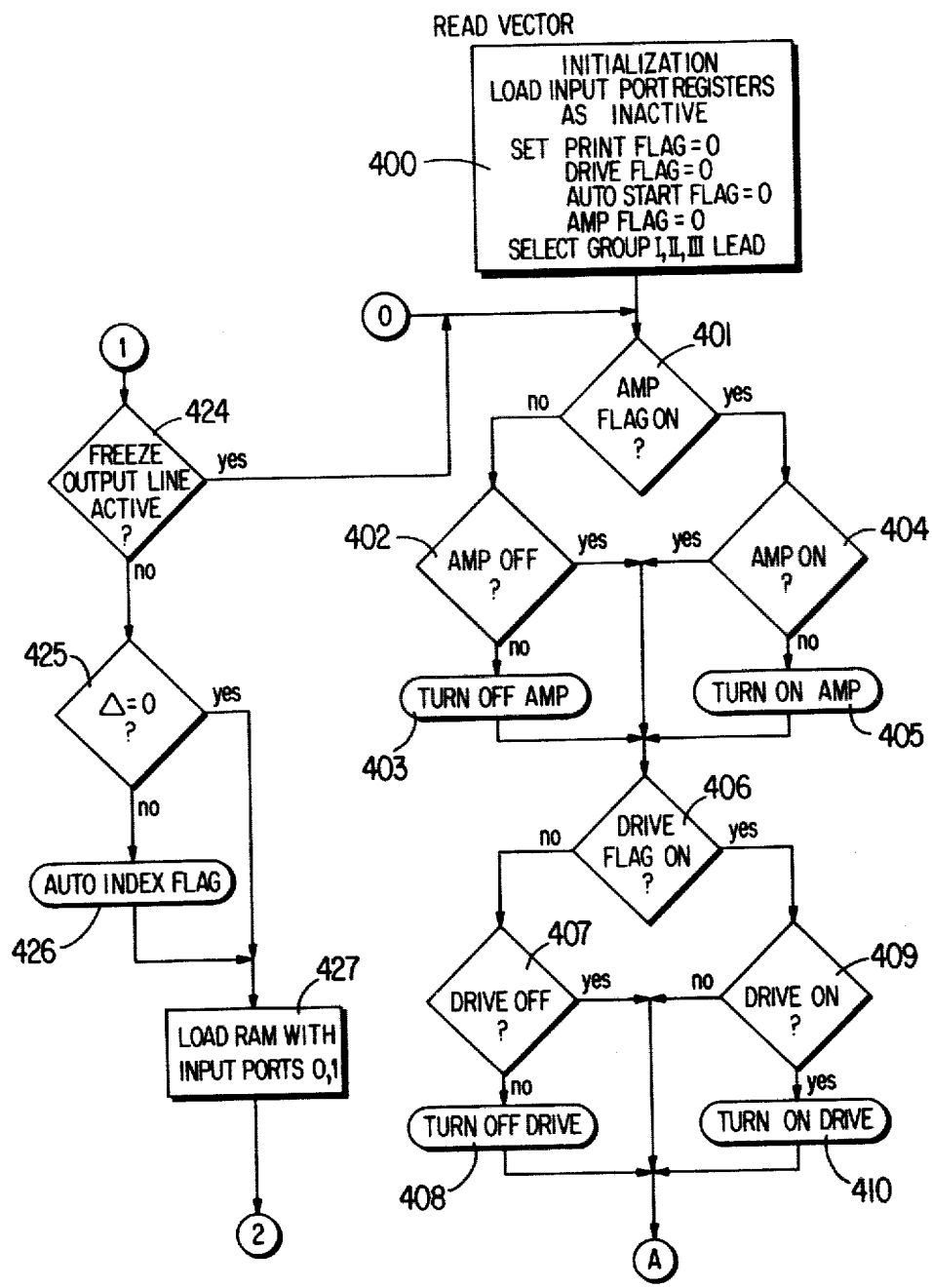

Specifically, FIG. 12A contains an initialization routine, and also pertains to the microprocessor control of the chart recording operations. Microprocessor 136 initializes the system by loading various input port registers with an "inactive" indication, clears various flags, and selects the Group I, II and III leads (block 400).

Microprocessor 136 then proceeds to check the amplifier and drive flags, and to appropriately turn on or turn off the amplifiers and drives, respectively (blocks 401 through 410).

Figure 12B:
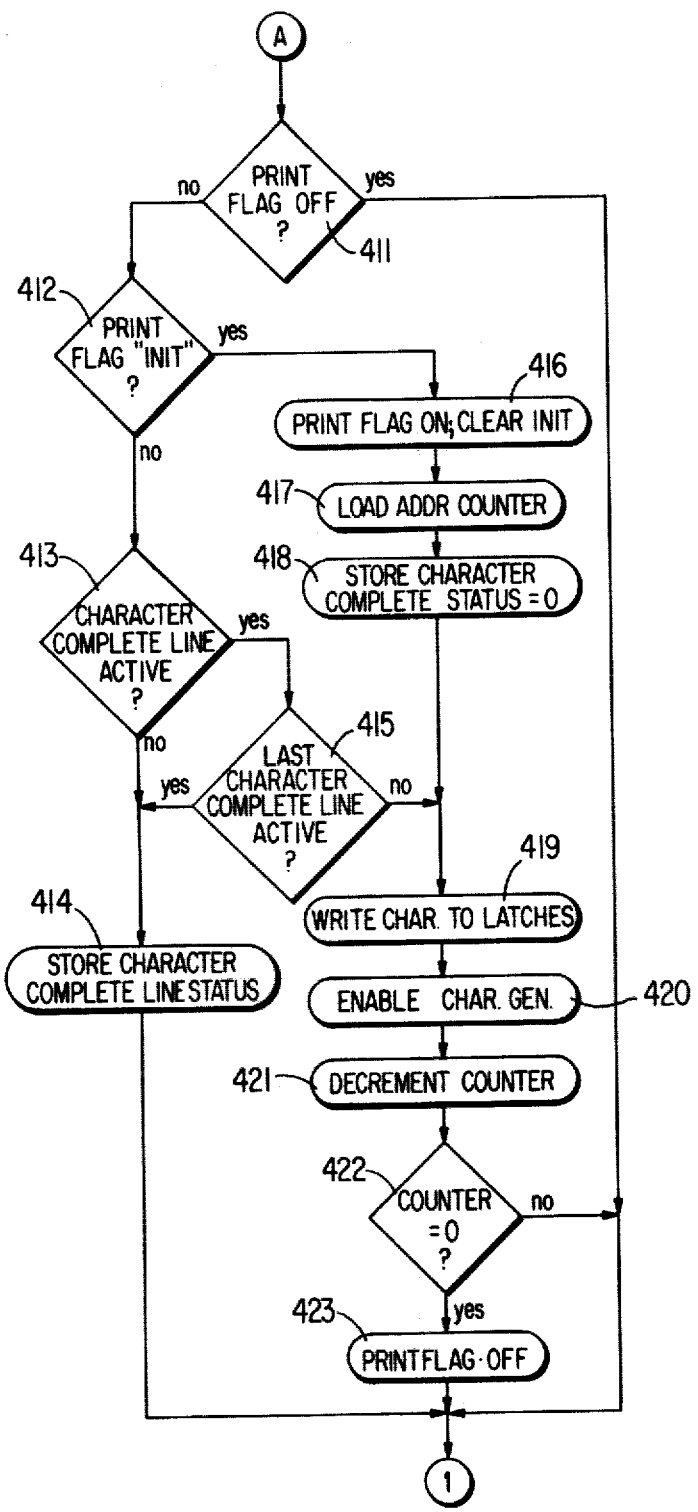

FIG. 12B pertains to microprocessor control of the alphanumeric printing operations performed by the chart recorder of the system. Initially, a check of the print flag is made (block 411): if the print flag is off, a branch back to FIG. 12A is executed; if it is on, this indicates that a printing operation is taking place, or is to take place. In that eventuality, a check of the print flag is made (block 412). If print flag is set to INIT, this indicates that printing is to be initiated, and various steps are taken (blocks 416 through 421) in order to initiate printing of the lead data on the chart passing through the chart recorder 62 (FIG. 1). A decision is them made as to whether or not a counter (a character counter which has been previously initialized to the number of alphanumeric characters to be printed) has achieved a zero count (block 422): if not, a branch to FIG. 12A is executed; if so, print flag is turned off (block 423), and the branch is executed.

Returning to block 412, if print flag was not set to INIT, a check of the character complete line is made (block 413). If it is not active, the character complete line status is stored (block 414), and the branch to FIG. 12A is executed. If character complete line is active, a check of the last character complete line is made (block 415). If the latter is active, the character complete line status is stored and the branch to FIG. 12A is executed; if the last character complete line is not active (indicating the completion of the previous character output), the operations of blocks 419 through 421 (relating to output of the next character) are executed, followed by decision block 422 (a check of the character counter), and execution of block 423 (if appropriate), followed by a branch to FIG. 12A.

Returning to FIG. 12A, a check of the freeze output line is performed (block 424). If active, a branch to previously discussed block 401 is executed; if not active, the freeze output line is checked for termination condition ("Delta" Status=0?—block 425). If delta freeze output line is not equal to zero, the auto index flag is set (block 426). In any event, a random access memory (associated with the microprocessor 136) is loaded with input ports 0, 1 (block 427), and a branch to FIG. 12C is executed.

Figure 12C:
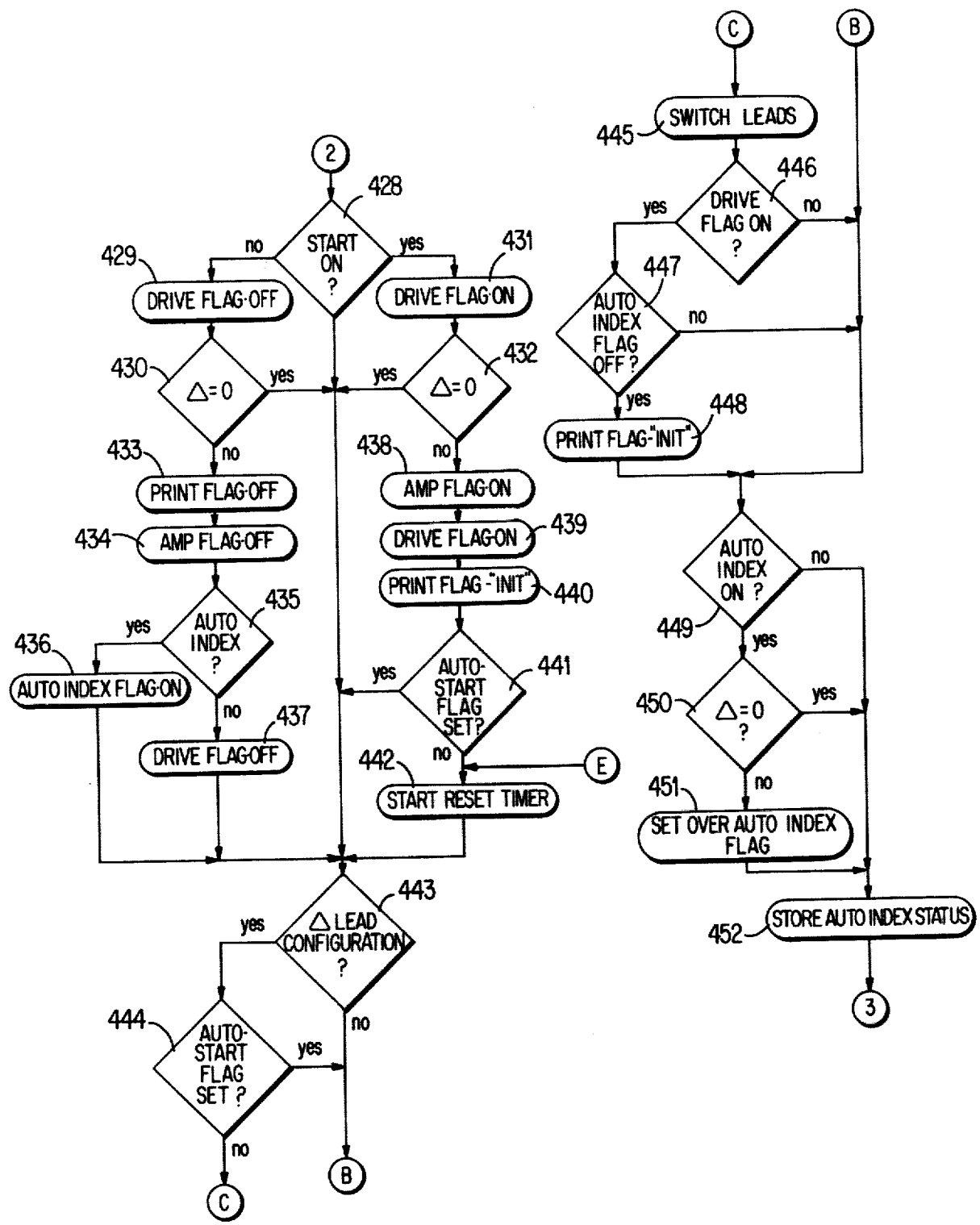

FIG. 12C contains a flowchart of the operations of microprocessor 136, the operations pertaining to setting of various flags and polling of various conditions to determine the mode of operation selected by the operator. Specifically, microprocessor 136 makes a check of the START flag (block 428), and turns off the drive flag (block 429) if START is off, followed by a decision as to whether or not the start flag was previously on (block 430). If "delta" is zero, a check of the change in lead configuration is made (block 443); if the lead configuration flag has not changed, the print flag and amplifier flag are turned off (blocks 433 and 434), and the system checks whether or not the "auto index" feature has been selected (block 435). If auto index has been selected, the auto index flag is turned on (block 436), and block 443 is executed; if not, the drive flag is turned off (block 437), and block 443 is then executed.

Returning to block 428, if START was on, the drive flag is turned on (block 431), followed by a check to see if the start flag was previously off (block 432). If the start flag has not changed, block 443 is executed; if it has changed, the amplifier flag and drive flag are turned on (blocks 438 and 439), and the print flag is set to INIT (block 440). This is followed by a check of the "auto start flag" (block 441). If set, block 443 is executed; if not set, the timer is started/reset. The latter functions pertain to the "auto cycle" function, by means of which the system automatically records data from predetermined lead groups for a predetermined time, repeating such recording at predetermined time intervals (as selected by the operator).

Referring to block 443, a check of change in lead configuration is made, and if there is a change in lead configuration, a further check of the "auto start flag" is made (block 444). If there was no change in the lead configuration, or if "auto start flag" was set, a branch to block 449 is executed. If the "auto start flag" was not set, a branch to block 445 is executed, that is, the microprocessor 136 switches leads. In other words, the microprocessor changes the control lines from the output port, and this changes the light on the front panel to the selected lead group and controls the switching network to direct the selected lead signal to the scope 40 and the chart recorder 62.

Continuing with the sequence, after the leads are switched, a check of the drive flag is performed (block 446). If the drive flag is on, a further check of the "auto index" flag is made (block 447), such that if the "auto index" flag is off, the print flag is set to INIT (block 448).

Further in the sequence, a check of "auto index" is made (block 449), and if it is on, a test is conducted to see if it was previously off (block 450). If it was off, the "over auto index flag" is set (block 451). In any event, the auto index status is stored (block 452), and a branch to FIG. 12D is executed.

Figure 12D:
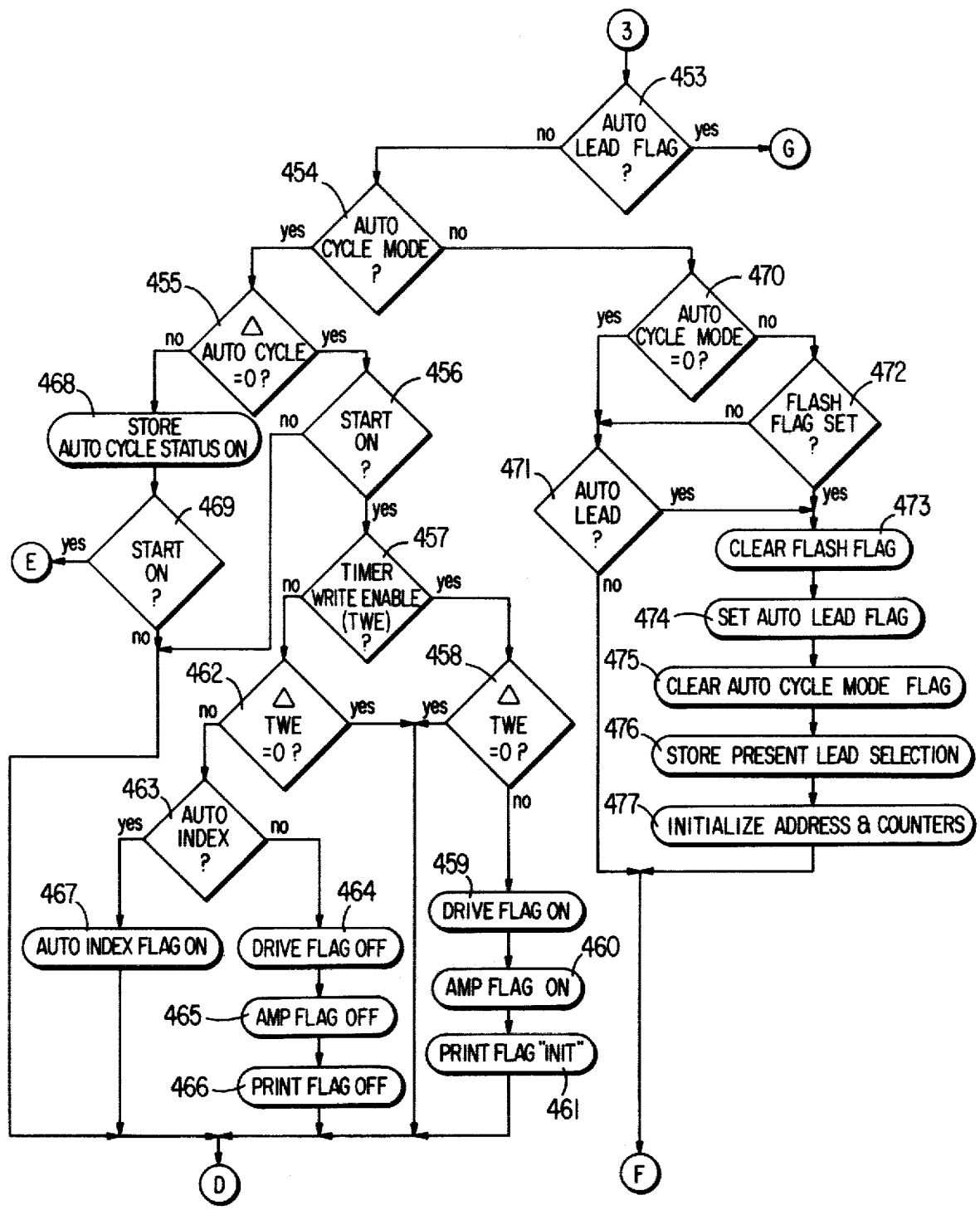

FIG. 12D contains a flowchart of those operations of the microprocessor 136 pertaining to the "auto cycle" and "auto lead" modes of operation.

Figure 12E:
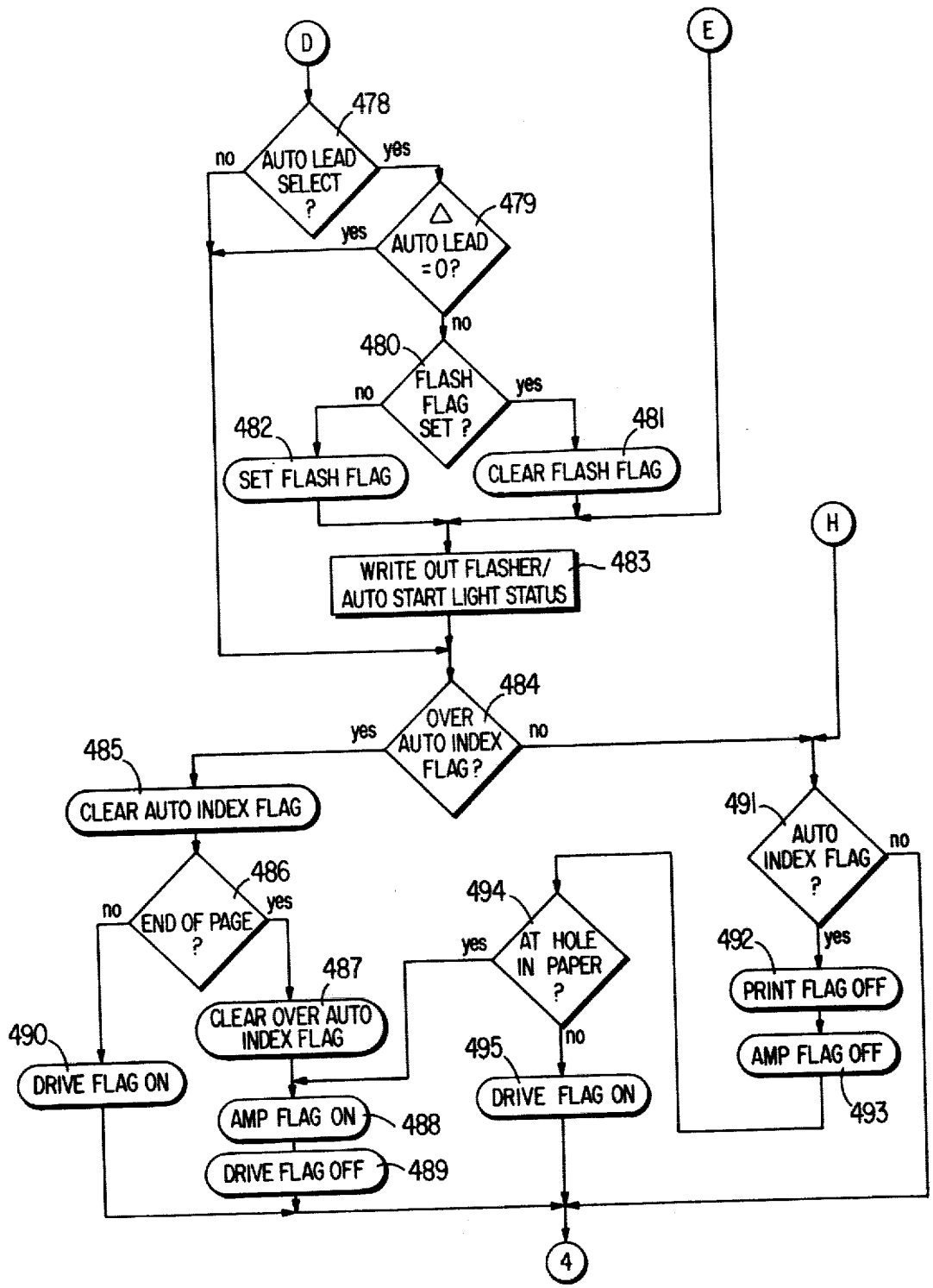
Figure 12G:
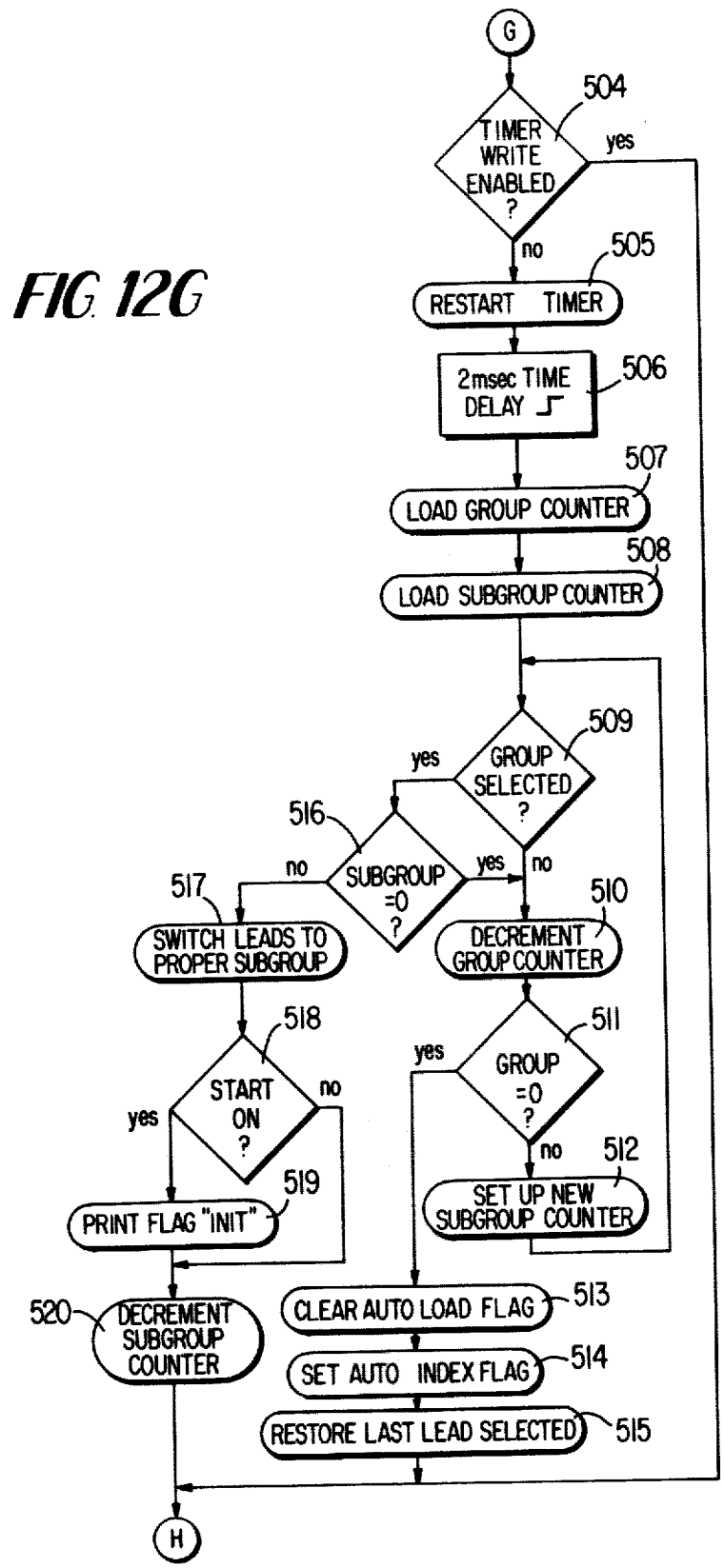

Referring to block 453, a check of the "auto lead" flag is made, and, if the flag is set, an immediate branch to FIG. 12G is executed. If not set, a check of the auto cycle mode (block 454) is made.

If the system is in the auto cycle mode, a check of delta auto cycle equals zero (block 455) is made. If delta auto cycle does not equal zero, auto cycle status is stored as "on" (block 468), and a check of "start" (block 469) is made. If start is "on", a branch back to block 442 of FIG. 12C is performed; if not on, a branch to FIG. 12E is performed.

Returning to block 455, if delta auto cycle equals zero, a check of "start" is made (block 456). If start is not on, a branch to FIG. 12E is performed; if start is on, a further check of timer write enable (block 457) is made. If timer write enable is not on, a further check to see if it was previously on is performed (block 462). If it was previously on, a check of auto index is made (block 463). If the "auto index" feature has been selected, the auto index flag is turned on (block 467), and a branch to FIG. 12E is executed; if "auto index" has not been selected, the drive, amplifier, and print flags are turned off (blocks 464 through 466), and the branch to FIG. 12E is executed.

Returning to block 457, if timer write enable is on, and was not previously off, (block 458), a branch to FIG. 12E is executed; if timer write enable is on, and the timer write enable flag was previously off, the driver and amplifier flags are turned on, the print flag is set to INIT (blocks 459 through 461), and a branch to FIG. 12E is executed.

Finally, referring back to block 454, if the auto cycle mode was not indicated, a check is made to see if the auto cycle mode was previously indicated (block 470). If it was not indicated, a further check of auto start is made (block 471). If auto start is not on, a branch to FIG. 12E is executed; if auto start is on, the flash and autocycle mode flags are cleared (blocks 473 and 475), the auto start flag is set (block 474), the present lead selection is stored (block 476), and the addresses and counters are initialized for the auto lead mode (block 477).

If the auto cycle mode was previously indicated (block 470), a check of the flash flag is performed (block 472). If the flash flag is not set, block 471 (check of auto start previously discussed) is executed; if flash flag is set, operations of blocks 473 through 477 (just discussed) are executed, and a branch to FIG. 12E is executed.

FIG. 12E contains a flowchart of the operations of the microprocessor 136 pertaining to "auto lead" and "auto index" features. Specifically, in block 478, a decision as to whether or not auto lead has been selected is made. If auto lead has not been selected, a branch to block 484 is executed; if auto lead has been selected, a further decision is made to see if auto lead was previously selected (block 479). If it was previously selected, block 484 is executed; if it was not, a check of the flash flag is made (block 480). If the flash flag is set, the flash flag is then cleared (block 481); conversely, if not set, the flash flag is set (block 482). The flasher and auto start light status are then written (block 483), and block 484 is then executed.

In block 484, a check as to the over auto index flag is made. If the over auto index flag is set, the auto index flag is cleared (block 485), followed by a decision as to whether or not an "end of page" condition has been detected (block 486). If not detected, the drive flag is turned on (block 490), and a branch to FIG. 12F is executed; if the "end of page" condition is detected, the over auto index flag is cleared (block 487), the amplifier flag is turned on (block 488), and the drive flag is turned off (block 489), followed by a branch to FIG. 12F.

Returning to block 484, if the over auto index flag is not set, a check of the auto index flag is made (block 491). If the auto index flag is not set, an immediate branch to FIG. 12F is executed; if the auto index flag is set, the print flag and amplifier flag are turned off (blocks 492 and 493), and a further decision as to whether or not the chart recorder has located a hole in the chart paper is made (block 494). If a hole in the paper has been detected, blocks 488 and 489 are executed (as previously described), and a branch to FIG. 12F is made; if a hole is not detected, the drive flag is turned on (block 495), and a branch to FIG. 12F is made.

FIG. 12F contains a series of checks of various flags and modes of operation: freeze select (block 496), auto index flag (block 497), auto cycle mode (block 498), and auto lead mode (block 499). If freeze select is requested, and if any one of auto index flag, auto cycle mode and auto lead mode are indicated, a branch to FIG. 12A, block 401 (that is, the beginning of the routine) is immediately executed. If freeze select is not requested, the immediate branch to FIG. 12A is executed. If freeze select is requested, and none of auto index flag, auto cycle mode and auto lead mode is indicated, a freeze pulse is provided as an output (block 500), the drive and amplifier flags are turned on (blocks 501 and 502), the print flag is set to INIT (block 503), a time delay for the freeze line is implemented (block 504), and the branch to FIG. 12A is then executed.

FIG. 12G contains a flowchart of those operations performed when the auto lead flag is set (see block 453 of FIG. 12D), indicating that the "auto lead" feature has been selected by the operator. A decision as to whether or not timer write is enabled is made (block 504). If enabled, an immediate branch to FIG. 12E is executed. If not enabled, the timer is restarted (block 505), a two millisecond time delay is introduced (block 506), the group counter is loaded (block 507), and the subgroup counter is loaded (block 508). Then, a decision as to whether or not a group has been selected is made (block 509). If not selected, the group counter is decremented (block 510), followed by a decision as to whether or not the parameter GROUP equals zero (block 511). If it equals zero, the auto lead flag is cleared (block 513), the auto index flag is set (block 514), and the last lead selected is restored (block 515), followed by a branch to FIG. 12E. If GROUP does not equal zero, a new subgroup counter is set up (block 512), and a return to block 509 is executed.

Further referring to block 509, if a group has been selected, a decision as to whether SUBGROUP equals zero is made (block 516). If equal to zero, the group counter is decremented (block 510), followed by previously discussed decision block 511; if SUBGROUP is not equal to zero, leads are switched to the proper subgroup (block 517), followed by a decision as to whether or not start is on (block 518). If start is on, the print flag is set to INIT (block 519); in any event, the subgroup counter is decremented (block 520), followed by a branch to FIG. 12E.

While preferred forms and arrangements have been shown in illustrating the invention, it is to be clearly understood that various changes in detail and arrangement may be made without departing from the spirit and scope of this disclosure.

We claim:

1. An electrocardiography system for displaying, in accordance with an operator input, electrocardiograph (ECG) data provided in a plurality of pickup leads, wherein said pickup leads in said plurality of pickup leads are divided into groups, said system comprising:
    selector means responsive to said operator input for selecting a corresponding group of said pickup leads;
    processing means for processing said ECG data from said corresponding group of said pickup leads to develop respective processed outputs;
    display means including a plurality of display channels for providing each one of said respective processed outputs on a corresponding one of said display channels in accordance with said operator input; and
    recording means including a plurality of recording channels for recording each said respective ECG data on a corresponding one of said recording channels in accordance with said operator input;
    wherein each said group comprises a predetermined number of said pickup leads, and wherein said plurality of display channels includes a given number of channels, equal in number to said predetermined number of said pickup leads, a spare channel, and operator actuator means for selecting one of said given number of channels and for actuating said spare channel to record thereon said respective ECG data from said selected one of said given number of channels;
    said system including switch means connected between said selector means and said display means, on the one hand, and said recording means, on the other hand, said switch means being responsive to said operator input for making a selection between said respective ECG data from each said pickup lead, said displayed respective ECG data from said display means, and said respective ECG data from said selected one of said given number of said channels as recorded on said spare channel, and for providing said selection to said recording means.

2. The system of claim 1, further comprising program monitor group select means for designating one of a plurality of program monitor groups and comprising individual pickup leads selected from various ones of said program monitor groups.

3. The system of claim 1, wherein said display means automatically displays said each one of said respective processed outputs for a predetermined time duration.

4. The system of claim 1, wherein said processing means comprises a plurality of ECG amplifiers, one for each pickup lead in said corresponding group of said pickup leads.

5. The system of claim 1, wherein said processing means comprises a plurality of gain filter units, one for each pickup lead in said corresponding group of said pickup leads, for gain-adjusting said ECG data received over said each pickup lead.

6. An electrocardiography system for displaying, in accordance with an operator input, electrocardiograph (ECG) data provided in a plurality of pickup leads, wherein said pickup leads in said plurality of pickup leads are divided into groups, said system comprising:
    selector means responsive to said operator input for selecting a corresponding group of said pickup leads, and for providing respective ECG data from each said pickup lead in said corresponding group of said pickup leads;
    display means including a plurality of display channels of a number equal to at least said number of pickup leads in said corresponding group of pickup leads for displaying each said respective ECG data on a corresponding one of said display channels in accordance with said operator input; and
    recording means including a plurality of recording channels for recording each said respective ECG data on a corresponding one of said recording channels in accordance with said operator input;
    wherein each said group comprises a predetermined number of said pickup leads, and wherein said plurality of display channels includes a given number of channels, equal in number to said predetermined number of said pickup leads, a spare channel, and operator actuator means for selecting one of said given number of channels and for actuating said spare channel to record thereon said respective ECG data from said selected one of said given number of channels;
    said system including switch means connected between said selector means and said display means, on the one hand, and said recording means, on the other hand, said switch means being responsive to said operator input for making a selection between said respective ECG data from each said pickup lead, said displayed respective ECG data from said display means, and said respective ECG data from said selected one of said given number of said channels as recorded on said spare channel, and for providing said selection to sid recording means.

7. The system of claim 6, said display means including freeze control means for freezing said respective ECG data from said selected one of said given number of channels as recorded on said spare channel.

8. An electrocardiography system for displaying, in accordance with an operator input provided via control console switches, electrocardiograph (ECG) data provided in a plurality of pickup leads, wherein said pickup leads in said plurality of pickup leads are divided into groups, said operator input designating a group of said pickup leads, said system comprising:
    lead switching means for receiving, selecting and switchably routing said ECG data from a group of said pickup leads designated by said operator input to provide a lead switching output;
    control means for processing said lead switching output to derive respective processed outputs; and display means including a plurality of display channels for displaying, as an output thereof, each one of said respective processed outputs on a corresponding one of said display channels in accordance with said operator input;

wherein said lead switching means comprises a lead switching unit connected to said plurality of pickup leads, and a plurality of amplifiers, one for each pickup lead in said group of pickup leads designated by said operator input, each of said plurality of amplifiers amplifying said ECG data from a respective lead in said group of pickup leads designated by said operator input so as to provide corresponding amplified outputs comprising said lead switching output;

wherein each of said plurality of amplifiers comprises a differential amplifier for receiving and amplifying a corresponding one of said received, selected and switchably routed ECG data from a corresponding one of said pickup leads of said group of said pickup leads designated by said operator input, said differential amplifier having two inputs and an output, threshold circuit means connected to said output of said differential amplifier for detecting an overvoltage in said output of said differential amplifier, and analog switch means responsive to detection by said threshold circuit means of said overvoltage for grounding said inputs of said differential amplifier until said overvoltage subsides.

9. The system of claim 8, wherein said control means generates control signals in response to said operator input, and wherein said lead switching unit comprises:

buffer means for buffering said ECG data from said pickup leads;

resistor network means for grouping said plurality of pickup leads and for electrically combining said ECG data from said plurality of pickup leads, so as to form a further plurality of ECG output signals;

a plurality of analog switches, one for each of said plurality of display channels, responsive to said operator input and to said control signals from said control means for selecting a corresponding one of said further plurality of ECG output signals, and for routing said selected corresponding one of said further plurality of ECG output signals to a corresponding one of said display channels designated by said operator input; and buffer means, one for each of said plurality of display channels, for buffering said selected and routed corresponding one of said further plurality of ECG output signals.

10. An electrocardiography system for displaying, in accordance with an operator input provided via control console switches, electrocardiograph (ECG) data provided in a plurality of pickup leads, wherein said pickup leads in said plurality of pickup leads are divided into groups, said operator input designating a group of said pickup leads, said system comprising:

lead switching means for receiving, selecting and switchably routing said ECG data from a group of said pickup leads designated by said operator input to provide a lead switching output;

control means for processing said lead switching output to derive respective processed outputs; and display means including a plurality of display channels for displaying, as an output thereof, each one of said respective processed outputs on a corresponding one of said display channels in accordance with said operator input;

wherein said lead switching means comprises a lead switching unit connected to said plurality of pickup leads, and a plurality of amplifiers, one for each pickup lead in said group of pickup leads designated by said operator input, each of said plurality of amplifiers amplifying said ECG data from a respective lead in said group of pickup leads designated by said operator input so as to provide corresponding amplified outputs comprising said lead switching output;

wherein each of said plurality of amplifiers comprises an analog switch for normally passing said ECG data to the output of said each of said plurality of amplifiers, and responsive to a control signal from said control means for blocking said ECG data and for passing a calibration signal to the output of said each of said plurality of amplifiers.

11. The system of claim 10, wherein said control means generates control signals in response to said operator input, and wherein said lead switching unit comprises:

buffer means for buffering said ECG data from said pickup leads;

resistor network means for grouping said plurality of pickup leads and for electrically combining said ECG data from said plurality of pickup leads, so as to form a further plurality of ECG output signals;

a plurality of analog switches, one for each of said plurality of display channels, responsive to said operator input and to said control signals from said control means for selecting a corresponding one of said further plurality of ECG output signals, and for routing said selected corresponding one of said further plurality of ECG output signals to a corresponding one of said display channels designated by said operator input; and buffer means, one for each of said plurality of display channels, for buffering said selected and routed corresponding one of said further plurality of ECG output signals.

12. An electrocardiography system for displaying, in accordance with an operator input provided via control console switches, electrocardiograph data provided in a plurality of pickup leads, wherein said pickup leads in said plurality of pickup leads are divided into groups, said operator input designating a group of said pickup leads, said system comprising:

lead switching means for receiving, selecting and switchably routing said ECG data from a group of said pickup leads designated by said operator input to provide a lead switching output;

control means for processing said lead switching output to derive respective processed outputs; and display means including a plurality of display channels for displaying, as an output thereof, each one of said respective processed outputs on a corresponding one of said display channels in accordance with said operator input;

wherein said lead switching means comprises a lead switching unit connected to said plurality of pickup leads, and a plurality of amplifiers, one for each pickup lead in said group of pickup leads designated by said operator input, each of said plurality of amplifiers amplifying said ECG data from a respective lead in said group of pickup leads designated by said operator input so as to provide corresponding amplified outputs comprising said lead switching output;

wherein said control means comprises:

gain adjust means for receiving and attenuating said lead switching output to develop corresponding attenuated outputs, said corresponding attenuated outputs being provided to respective ones of said plurality of amplifiers in said lead switching means;

said respective ones of said plurality of amplifiers each comprising a first differential amplifier for filtering in accordance with a first frequency to provide a first filtered output, and a second differential amplifier for filtering in accordance with a second frequency to provide a second filtered output;

said control means further comprising switch means receiving said first and second filtered outputs and being responsive to said operator input for selectively providing one of said first and second filtered outputs as an output of said switch means;

said output of said switch means comprising said respective processed outputs of said control means;

said control means further comprising direct/delay switching means for receiving said output of said switch means and said output of said display means, and being responsive to said operator input for selectively providing at least one of said output of said switch means and said output of said display means as a further plurality of respective processed outputs of said control means for recording.

13. The system of claim 12, wherein said gain adjust means comprises a plurality of selectable resistors for electrically processing said lead switching output.

14. The system of claim 12, said control means comprising a control circuit responsive to said operator input for automatically generating a calibration output provided to each of said plurality of amplifiers, whereby to provide a calibration signal in each of said display channels.

15. The system of claim 12, said control means comprising a control circuit responsive to said operator input for automatically and periodically generating a calibration output provided to each of said plurality of amplifiers, whereby to provide a periodic calibration signal in each of said display channels.

16. The system of claim 12, said control means further comprising a processor and a processor interface unit, said processor interface unit receiving said operator input, said operator input designating operator selection of said plurality of pickup leads providing ECG data for display, said processor interface unit including an encoder responsive to said operator input for providing a corresponding digital coded output to said processor.

17. The system of claim 12, said system comprising a chart recorder for recording said each one of said respective processed outputs on a corresponding recording track on chart paper moving through said chart recorder, said chart paper comprising a plurality of sheets, each having a beginning portion, said control means further comprising a processor and a processor interface unit, said processor controlling said chart recorder to move said paper therethrough, said processor interface unit comprising means for sensing the beginning portion of each said sheet of said chart paper and providing a detection signal to said processor, said processor being responsive thereto for stopping said chart paper at the beginning portion of said sheet.

18. The system of claim 12, said control means further comprising a processor and a processor interface unit, said processor being responsive to said operator input for providing a decoded output indicating said group of pickup leads designated by said operator input, said processor interface unit including decoder circuitry responsive to said decoded output of said processor for providing corresponding driver signals, one for each of said group of pickup leads which can be designated by said operator input, said system including a control console having group indicator lamps, said decoding means providing said corresponding driver output signal to a corresponding one of said group indicator lamps for indicating to the operator the selected group.

19. The system of claim 12, wherein said operator input includes an auto lead signal designating operator selection of a first mode of operation, said first mode of operation comprising selective and successive display by said system of ECG data from a predetermined set of groups of pickup leads, said operator input further comprising an auto cycle selection signal designating operator selection of a second mode of operation, said second mode of operation comprising continuous automatic display of said ECG data from said group of pickup leads designated by said operator input, said control means further comprising a processor and a processor interface unit, said processor being responsive to said auto lead selection signal and said auto cycle selection signal for producing corresponding first and second control outputs, said system including a control console having an auto lead lamp for indicating when said operator has selected said first mode of operation, said processor interface unit being responsive to said first control output for continuously lighting said auto lead lamp, said processor being responsive to said auto cycle selection signal for disabling said first mode of operation, said processor interface unit being responsive to said second control output of said processor for blinking said auto lead lamp, whereby to indicate disabling of said first mode of operation.

20. The system of claim 12, wherein said control means comprises a processor for providing control signals indicating said group of pickup leads for which ECG data is being displayed, said system further comprising a chart recorder, said control means further comprising a character generator responsive to said control signals from said microprocessor for actuating said chart recorder to print identification of said group of pickup leads for which ECG data is being displayed.

21. The system of any one of claims 8, 10 or 12, further comprising program monitor group select means responsive to said operator input for designating a plurality of pickup leads comprising a special monitor group selected by the operator.

22. The system of claim 21, said system including control console switches indicating operator selection of a plurality of pickup leads comprising a program monitor group selected by the operator, said control console switches being responsive to said operator selection for issuing control signals, said program monitor group select means including at least one encoder for receiving and encoding said control signals from said control console switches, and issuing a monitor lead code for each selected pickup lead in said special monitor group, said console switches being further settable by the operator to designate display channels selected by the operator for display of said selected pickup leads, said program monitor group select means including logic means responsive to said selection of display channels by the operator for producing a coded output corresponding thereto, said program monitor group select means further comprising a comparator circuit for comparing the various channels selected by the operator for display of the selected pickup leads, said comparator circuit being responsive to selection by the operator of the same channel for display of a plurality of pickup leads for issuing a disable signal disabling said logic means from encoding said channel selection by said operator.

23. The system of claim 12, said control means receiving said operator input, said operator input comprising an auto cycle selection signal indicating operator selection of an auto cycle mode of operation and a selected delay time between recordings, said operating input also including a selected recording time in said auto cycle mode of operation, said control means including a processor responsive to said auto cycle selection signal for successively issuing a reset signal and a start signal, said control means including a timer/counter responsive to said reset signal for being placed in a reset state, and being responsive to said start signal so as to count through a first time interval corresponding to said recording time so as to generate a first output, and said timer/counter counting through a second time interval corresponding to said delay time between recordings so as to issue a second output.

24. An electrocardiography system for recording, in accordance with an operator input provided via control console switches, electrocardiograph (ECG) data provided in a plurality of pickup leads, wherein said pickup leads in said plurality of pickup leads are divided into groups, said operator input designating a group of said pickup leads, said system comprising:
lead switching means for receiving, selecting and switchably routing said ECG data from a group of said pickup leads designated by said operator input to provide a lead switching output;
control means for processing said lead switching output to derive respective processed outputs; and
recording means including a plurality of recording channels for recording, as an output thereof, each one of said respective processed outputs on a corresponding one of said recording channels in accordance with said operator input, said control means receiving said operator input, said operator input comprising an auto cycle selection signal indicating operator selection of an auto cycle mode of operation and a selected delay time between recordings, said operator input also including a selected recording time in said auto cycle mode of operation, said control means including a processor responsive to said auto cycle selection signal for successively issuing a reset signal and a start signal, said control means including a timer/counter responsive to said reset signal for being placed in a reset state, and being responsive to said start signal so as to count through a first time interval corresponding to said recording time so as to generate a first output, and said timer/counter counting through a second time interval corresponding to said delay time between recordings so as to issue a second output.

25. The system of claim 24, said control means further comprising means responsive to alteration of at least one of said delay time between recordings and said recording time of said operator input for resetting and restarting said timer/counter.

26. An electrocardiography system for recording, in accordance with an operator input provided via control console switches, electrocardiograph (ECG) data provided in a plurality of pickup leads, wherein said pickup leads in said plurality of pickup leads are divided into groups, said operator input designating a group of said pickup leads, said system comprising:
lead switching means for receiving, selecting and switchably routing said ECG data from said group of said pickup leads designated by said operator input to provide a lead switching output;
control means responsive to said operator input for processing said lead switching output to derive respective processed outputs; and
recording means including a plurality of recording channels for recording each one of said respective processed outputs on a corresponding one of said recording channels in accordance with said operator input;
wherein said lead switching means comprises a lead switching unit connected to said plurality of pickup leads, and a plurality of amplifiers, one for each pickup lead in said group of pickup leads designated by said operator input, each of said plurality of amplifiers amplifying said ECG data from a respective lead in said group of pickup leads designated by said operator input so as to provide corresponding amplified outputs comprising said lead switching output;
wherein each of said plurality of amplifiers comprises a differential amplifier for receiving and amplifying a corresponding one of said received, selected and switchably routed ECG data from a corresponding one of said pickup leads of said group of pickup leads designated by said operator input, said differential amplifier having two inputs and an output, threshold circuit means connected to said output of said differential amplifier for detecting an overvoltage in said output of said differential amplifier, and analog switch means responsive to detection by said threshold circuit means of said overvoltage for grounding said inputs of said differential amplifier until said overvoltage subsides.

27. The system of claim 26, wherein said control means generates control signals in response to said operator input, and wherein said lead switching unit comprises:
buffer means for buffering said ECG data from said pickup leads;
resistor network means for grouping said plurality of pickup leads and for electrically combining said ECG data from said plurality of pickup leads, so as to form a further plurality of ECG output signals;
a plurality of analog switches, one for each of said plurality of recording channels, responsive to said operator input and to said control signals from said control means for selecting a corresponding one of said further plurality of ECG output signals, and for routing said selected corresponding one of said further plurality of ECG output signals to a corresponding one of said recording channels designated by said operator input; and
buffer means, one for each of said plurality of recording channels, for buffering said selected and routed corresponding one of said further plurality of ECG output signals.

28. An electrocardiography system for recording, in accordance with an operator input provided via control console switches, electrocardiograph (ECG) data provided in a plurality of pickup leads, wherein said pickup leads in said plurality of pickup leads are divided into groups, said operator input designating a group of said pickup leads, said system comprising:

lead switching means for receiving, selecting and switchably routing said ECG data from said group of said pickup leads designated by said operator input to provide a lead switching output;

control means responsive to said operator input for processing said lead switching output to derive respective processed outputs; and recording means including a plurality of recording channels for recording each one of said respective processed outputs on a corresponding one of said recording channels in accordance with said operator input;

wherein said lead switching means comprises a lead switching unit connected to said plurality of pickup leads, and a plurality of amplifiers, one for each pickup lead in said group of pickup leads designated by said operator input, each of said plurality of amplifiers amplifying said ECG data from a respective lead in said group of pickup leads designated by said operator input so as to provide corresponding amplified outputs comprising said lead switching output;

wherein each of said plurality of amplifiers comprises an analog switch for normally passing said ECG data to the output of said each of said plurality of amplifiers, and responsive to a control signal from said control means for blocking said ECG data and for passing a calibration signal to the output of said each of said plurality of amplifiers.

29. The system of claim 28, wherein said control means generates control signals in response to said operator input, and wherein said lead switching unit comprises:

buffer means for buffering said ECG data from said pickup leads;

resistor network means for grouping said plurality of pickup leads and for electrically combining said ECG data from said plurality of pickup leads, so as to form a further plurality of ECG output signals;

a plurality of analog switches, one for each of said plurality of recording channels, responsive to said operator input and to said control signals from said control means for selecting a corresponding one of said further plurality of ECG output signals, and for routing said selected corresponding one of said further plurality of ECG output signals to a corresponding one of said recording channels designated by said operator input; and buffer means, one for each of said plurality of recording channels, for buffering said selected and routed corresponding one of said further plurality of ECG output signals.

30. An electrocardiography system for recording, in accordance with an operator input provided via control console switches, electrocardiograph (ECG) data provided in a plurality of pickup leads, wherein said pickup leads in said plurality of pickup leads are divided into groups, said operator input designating a group of said pickup leads, said system comprising:

lead switching means for receiving, selecting and switchably routing said ECG data from said group of said pickup leads designated by said operator input to provide a lead switching output;

control means responsive to said operator input for processing said lead switching output to derive respective processed outputs; and recording means including a plurality of recording channels for recording each one of said respective processed outputs on a corresponding one of said recording channels in accordance with said operator input;

wherein said lead switching means comprises a lead switching unit connected to said plurality of pickup leads, and a plurality of amplifiers, one for each pickup lead in said group of pickup leads designated by said operator input, each of said plurality of amplifiers amplifying said ECG data from a respective lead in said group of pickup leads designated by said operator input so as to provide corresponding amplified outputs comprising said lead switching output;

said system further comprising display means for displaying, as an output thereof, said each one of said respective processed outputs, and wherein said control means comprises:

gain adjust means for receiving and attenuating said lead switching output to develop corresponding attenuated outputs, said corresponding attenuated outputs being provided to respective ones of said plurality of amplifiers in said lead switching means;

said respective ones of said plurality of amplifiers each comprising a first differential amplifier for filtering in accordance with a first frequency to provide a first filtered output, and a second differential amplifier for filtering in accordance with a second frequency to provide a second filtered output;

said control means further comprising switch means receiving said first and second filtered outputs and being responsive to said operator input for selectively providing one of said first and second gain filtered outputs as an output of said switch means;

said output of said switch means comprising said respective processed outputs of said control means;

said control means further comprising direct/delay switching means for receiving said output of said switch means and said output of said display means, and being responsive to said operator input for selectively providing at least one of said output of said switch means and said output of said display means as a further plurality of respective processed outputs of said control means for recording.

31. The system of claim 30, wherein said gain adjust means comprises a plurality of selectable resistors for electrically processing said lead switching output.

32. The system of claim 30, said control means comprising a control circuit responsive to said operator input for automatically generating a calibration output provided to each of said plurality of amplifiers, whereby to provide a calibration signal in each of said recording channels.

33. The system of claim 30, said control means comprising a control circuit responsive to said operator input for automatically and periodically generating a calibration output provided to each of said plurality of amplifiers, whereby to provide a periodic calibration signal in each of said recording channels.

34. The system of claim 30, said control means further comprising a processor and a processor interface unit, said processor interface unit receiving said operator input, said operator input designating operator selection of said plurality of pickup leads providing ECG data for recording, said processor interface unit including an encoder responsive to said operator input for providing a corresponding digital coded output to said processor.

35. The system of claim 30, said system comprising a chart recorder for recording said each one of said respective processed outputs on a corresponding recording track on chart paper moving through said chart recorder, said chart paper comprising a plurality of sheets, each having a beginning portion, said control means further comprising a processor and a processor interface unit, said processor controlling said chart recorder to move said paper therethrough, said processor interface unit comprising means for sensing the beginning portion of each said sheet of said chart paper and providing a detection signal to said processor, said processor being responsive thereto for stopping said chart paper at the beginning portion of said sheet.

36. The system of claim 30, said control means further comprising a processor and a processor interface unit, said processor being responsive to said operator input for providing a decoded output indicating said group of pickup leads designated by said operator input, said processor interface unit including decoder circuitry responsive to said decoded output of said processor for providing corresponding driver signals, one for each of said group of pickup leads which can be designated by said operator input, said system including a control console having group indicator lamps, said decoding means providing said corresponding driver output signal to a corresponding one of said group indicator lamps for indicating to the operator the selected group.

37. The system of claim 36, said system including control console switches indicating operator selection of a plurality of pickup leads comprising a program monitor group selected by the operator, said control console switches being responsive to said operator selection for issuing control signals, said program monitor group select means including at least one encoder for receiving and encoding said control signals from said control console switches, and issuing a monitor lead code for each selected pickup lead in said special monitor group, said console switches being further settable by the operator to designate display channels selected by the operator for display of said selected pickup leads, said program monitor group select means including logic means responsive to said selection of display channels by the operator for producing a coded output corresponding thereto, said program monitor group select means further comprising a comparator circuit for comparing the various channels selected by the operator for display of the selected pickup leads, said comparator circuit being responsive to selection by the operator of the same channel for display of a plurality of pickup leads for issuing a disable signal disabling said logic means from encoding said channel selection by said operator.

38. The system of claim 30, wherein said operator input includes an auto lead signal designating operator selection of a first mode of operation, said first mode of operation comprising selective and successive recording by said system of ECG data from a predetermined set of groups of pickup leads, said operator input further comprising an auto cycle selection signal designating operator selection of a second mode of operation, said second mode of operation comprising periodic recording to said ECG data from said group of pickup leads designated by said operator input, said control means further comprising a processor and a processor interface unit, said processor being responsive to said auto lead selection signal and said auto cycle selection signal for producing corresponding first and second control outputs, said system including a control console having an auto lead lamp for indicating when said operator has selected said first mode of operation, said processor interface unit being responsive to said first control output for continuously lighting said auto lead lamp, said processor being responsive to said autocycle selection signal for disabling said first mode of operation, said processor interface unit being responsive to said second control output of said processor for blinking said auto lead lamp, whereby to indicate disabling of said first mode of operation.

39. The system of claim 30, wherein said control means comprises a process for providing control signals indicating said group of pickup leads for which ECG data is being recorded, said system further comprising a chart recorder, said control means further comprising a character generator responsive to said control signals from said microprocessor for actuating said chart recorder to print identification of said group of pickup leads for which ECG data is being recorded.

40. The system of any one of claims 26, 28 or 30, further comprising program monitor group select means responsive to said operator input for designating a a special monitor group selected by the operator, whereby the operator may select pickup leads from various different groups to define said special monitor group.

41. The system of claim 30, said control means receiving said operator input, said operator input comprising an auto cycle selection signal indicating operator selection of an auto cycle mode of operation and a selected delay time between recordings, said operator input also including a selected recording time in said auto cycle mode of operation, said control means including a processor responsive to said auto cycle selection signal for successively issuing a reset signal and a start signal, said control menas including a timer/counter responsive to said reset signal for being placed in a reset state, and being responsive to said start signal so as to count through a first time interval corresponding to said recording time so as to generate a first output, and said timer/counter counting through a second time interval corresponding to said delay time between recordings so as to issue a second output.

42. An electrocardiography system for recording, in accordance with an operator input provided via control console switches, electrocardiograph (ECG) data provided in a plurality of pickup leads, wherein said pickup leads in said plurality of pickup leads are divided into groups, said operator input designating a group of said pickup leads, said system comprising:
  lead switching means for receiving, selecting and switchably routing said ECG data from said group of said pickup leads designated by said operator input to provide a lead switching output;
  control means responsive to said operator input for processing said lead switching output to derive respective processed outputs; and
  recording means including a plurality of recording channels for recording each one of said respective processed outputs on a corresponding one of said recording channels in accordance with said operator input, said control means receiving said operator input, said operator input comprising an auto cycle selection signal indicating operator selection of an auto cycle mode of operation and a selected delay time between recordings, said operator input also including a selected recording time in said auto cycle mode of operation, said control means including a processor responsive to said auto cycle selection signal for successively issuing a reset signal and a start signal, said control means including a timer/counter responsive to said reset signal for being placed in a reset state, and being responsive to said start signal so as to count through a first time interval corresponding to said recording time so as to generate a first output, and said timer/counter counting through a second time interval corresponding to said delay time between recordings so as to issue a second output.

43. The system of claim 42, said control means further comprising means responsive to alteration of at least one of said delay time between recordings and said recording time of said operator input for resetting and restarting said timer/counter.

* * * * *